(12) United States Patent
Henderson et al.

(10) Patent No.: US 7,351,744 B2
(45) Date of Patent: Apr. 1, 2008

(54) NAPHTHALENE DERIVATIVES AS TERMITE REPELLENTS AND TOXICANTS

(75) Inventors: Gregg Henderson, St. Gabriel, LA (US); Sanaa A. Ibrahim, Baton Rouge, LA (US); Rosemary Patton, Lake Charles, LA (US); Roger A. Laine, Baton Rouge, LA (US); Betty C. R. Zhu, Baton Rouge, LA (US); Feng Chen, Central, SC (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 712 days.

(21) Appl. No.: 10/641,315

(22) Filed: Aug. 14, 2003

(65) Prior Publication Data
US 2005/0037045 A1 Feb. 17, 2005

(51) Int. Cl.
*A01N 35/00* (2006.01)
(52) U.S. Cl. .................. 514/682; 424/84; 424/405; 424/406; 424/DIG. 11; 514/717
(58) Field of Classification Search .............. None
See application file for complete search history.

(56) References Cited

U.S. PATENT DOCUMENTS

| | | | |
|---|---|---|---|
| 4,107,066 A | 8/1978 | Schreiber et al. | 252/132 |
| 4,788,341 A | 11/1988 | Zoeller | 568/315 |
| 4,921,696 A | 5/1990 | Vander Meer et al. | 424/84 |
| 5,303,523 A | 4/1994 | Hand et al. | 52/101 |
| 5,609,879 A | 3/1997 | Myles | 424/410 |
| 5,637,298 A * | 6/1997 | Stowell | 424/84 |
| 5,802,779 A | 9/1998 | Hulls et al. | 52/101 |
| 5,874,097 A | 2/1999 | Henderson et al. | 424/405 |

(Continued)

FOREIGN PATENT DOCUMENTS

JP    2533880    * 9/1996

OTHER PUBLICATIONS

Ibrahim, S.A. et al., "Toxic and repellent effects of 2'-acetonaphthone on *Coptotermes formosanus* (Isoptera: Rhinotermitidae)," submitted to Pest Management Science, Jun. 6, 2003.

(Continued)

*Primary Examiner*—Neil S. Levy
(74) *Attorney, Agent, or Firm*—John H. Runnels; Bonnie J. Davis

(57) ABSTRACT

Several derivatives of naphthalene, including 1'-acetonaphthone, 2'-acetpnaphthone, 1-methoxynaphthalene, and 2-methoxynaphthalene, were discovered to be effective toxicants and repellents of termites, and resulted in significant reduction in termite feeding activity. For example, 2'-acetonaphthone was found to be an effective repellent and feeding deterrent of termites. Termites exposed to concentrations as low as 8 mg/kg sand exhibited a significant reduction in tunneling and feeding activity. Moreover, some of the dead termites had symptoms indicative of a failure to molt. At concentrations $\geq 20$ µg/cm$^2$, 2'-acetonaphthone was a strong repellent. Interestingly, at 160-fold lower concentration (0.125 µg/cm$^2$), 2'-acetonaphthone stimulated termite feeding activity. As a sand barrier, 2'-acetonaphthone significantly inhibited tunneling and feeding activity in concentrations from 8.33 to 35.0 mg/kg. Molting problems were also identified in termites exposed to 2'-acetonaphthone.

8 Claims, 11 Drawing Sheets

U.S. PATENT DOCUMENTS 6,352,703 B1 * 3/2002 Henderson et al. .......... 424/406

OTHER PUBLICATIONS

Ibrahim, S.A. et al., "Tunneling and feeding behaviors of *Coptotermes formosanus* (Isoptera: Rhinotermitidae) in response to 2'-acetonaphthone -treated sand," submitted to Pest Management Science, Apr. 2, 2003.

Agency for Toxic Substances and Disease Registry (ATSDR), Toxicological profile for naphthalene, 1-methylnaphthalene and 2-methylnaphthalene, Atlanta, GA: U.S. Dept. of Health and Human Services, Public Health Service (1995).

Chen, J. et. al., "Isolation and identification of 2-phenoxyethanol from ballpoint pen as a trail-following substance of *Coptotermes formosanus* Shiraki and *Reticulitermes* spp.", J. Entomol. Sci., vol. 33, pp. 97-105 (1998).

Chen, J. et al., "Termites fumigate their nests with naphthalene," Nature, vol. 392, pp. 558 (1998).

Grace, J.K. et. al., "Behavioral effects of a neem insecticide on *Coptotermes formosanus* (Isoptera: Rhinotermitidae)," *Trop Pest Manage*, 38: 176-180 (1992).

Grace, J.K., "Natural resistance of Alaska-cedar, redwood, and teak to Formosan subterranean termites," Forest Products Journal, vol. 44, pp. 41-45 (1994).

Ibrahim, S.A. et al., Toxic and Repellent Effects of 2'-Acetonaphthone on *Coptotermes formosanus* (Isoptera: Rhinotermitidae), submitted to Sociobiology (in Press) (2004).

Ibrahim, S.A. et al., "Survivorship, tunneling and feeding behaviors of *Coptotermes formosanus* (Isoptera: Thinotermitidae) in response to 2'-acetonaphthone-treated sand," submitted to Pest Management Science (in Press) (2004).

Katsura, E. et. al., Indoor air pollution by Chlorpyrifos and S-421 after Application for Termite Control, *Japanese J. Toxicol. Environ. Health*, vol. 42, No. 4, pp. 354-359 (1996).

Lin, Tien-shu et al., "The effects of *Cinnamomum* spp. Oils on the control of termite *Coptotermes formosanus* Shiraki," Taiwan For. Res. Inst. New Series, vol. 10 pp. 459-464 (1995).

Maistrello, L. et al., "Effects of nootkatone and a borate compound on Formosan subterranean termites (Isoptera: Rhinotermitidae) and its symbiont protozoa," J. Enotmol. Sci., vol. 36, pp. 229-236 (2001).

Maistrello, L. et al., Efficacy of vetiver oil and nootkatone as soil barriers against Formosan subterranean termite (Isoptera: Rhinotermitidae), to *J. Econ. Entomol.*, vol. 94, pp. 1532-1557 (2001).

Osbrink, W.L.A. et. al, Insecticide susceptibility in *Coptotermes formosanus* and *Reticulitermus virginicus* ( Isoptera: Rhinotermitidae), *J Entomol Sci.*, vol. 90, pp. 1217-1228 (2001).

Su, N-Y et. al., Comparison of tunneling responses into insecticide-treated soil by field populations and laboratory groups of subterranean termites, *J. Econ. Entomol.*, 90: 503-509 (1997).

Supriana, N., "Preliminary tests on the effects of naturally occurring chemicals on termites," Document IRG/WP/1181, The International Research Group on Wood Preservation, Queensland, Australia, 11 pp (1983).

Wilkins, C.K., "Naturally occurring anti-termite compounds," *Mater. Org*, 27:47-66 (1992).

Zhu, B.C.R. et al., Evaluation of vetiver oil and seven insect-active essential oils against Formosan subterranean termites, submitted to *J. Chem.*, vol. 27, pp. 1617-1625 (2001).

Zhu, B.C.R. et al., Nootkatone is a repellent for Formosan subterranean termite (*Coptotermes formosanus*), *J Chem Ecol*, 27: 523-531 (2001).

\* cited by examiner

NAPHTHALENE DERIVATIVES AS TERMITE REPELLENTS AND TOXICANTS

The development of this invention was partially funded by the Government under a grant from the United States Department of Agriculture. The Government has certain rights to this invention.

This invention pertains to the use of derivatives of naphthalene, especially 1' and 2'-acetonaphthone and 1 and 2-methoxynaphthalene, as repellents and toxicants to termites, e.g., the Formosan subterranean termite.

The genus *Coptotermes* contains the largest number of termite pests (28 species) among the 2,500 termite species worldwide. Of all subterranean termite species, *Coptotermes formosanus* Shiraki is the most widely distributed, and is considered one of the most economically destructive pests in the United States, particularly in states with hot and humid weather. In the U.S., over one billion dollars are spent annually on termite prevention and control, and on repairs due to termite damage.

A single colony of Formosan subterranean termites may contain several million individual termites. By comparison, the size of a colony of the native U.S. termite species is about one-tenth that of Formosan termites. *C. formosanus* attacks both living trees and structural wood, and can form colonies that do not touch the ground. Formosan subterranean termites, once established in an area, have never been eradicated.

Four principal methods have been used in the past to control termites species: (1) chemical and physical barriers to prevent termites from reaching wood; (2) wood preservatives and termiticides to protect infested or susceptible wood; (3) destruction of the termite colony by excavation of the nest; and (4) using slow-acting toxic baits. See, for example, U.S. Pat. Nos. 4,921,696; 5,303,523; 5,609,879; 5,802,779; and 5,874,097.

The extensive use of chemical barriers and termiticides have generated concern over environmental safety, especially use of synthetic insecticides. See, e.g., E. Katsura et. al., "Indoor air pollution by chlorpyrifos and S-421 after application for termite control," *Japanese Journal of Toxicology and Environmental Health*, vol. 42, pp. 354-359 (1996). In addition, the potential for increasing termite tolerance to insecticides is a concern. See, e.g., N-Y Su et. al., "Comparison of tunneling responses into insecticide-treated soil by field populations and laboratory groups of subterranean termites," *J. Econ. Entomol.*, vol. 90, pp. 503-509 (1997). See, e.g., W. L. A. Osbrink et. al, "Insecticide susceptibility in *Coptotermes formosanus* and *Reticulitermes virginicus* (Isoptera: Rhinotermitidae)," *J. Entomol. Sci.*, vol. 94, pp. 1217-1228 (2001).

Termite control programs usually require insecticide applications nearby or inside homes. Therefore, any control agent must be carefully screened to minimize the side-effects to human health, other non-target organisms, and the environment. Natural products from some essential oils have been evaluated for their use in controlling termites because of the belief that the environmental impact would be less than synthetic chemicals. See, e.g., N. Supriana, "Preliminary tests on the effects of naturally occurring chemicals on termites," Document IRG/WP/1181, The International Research Group on Wood Preservation, Queensland, Australia, 11 pp (1983); J. K. Grace et. al., "Behavioral effects of a neem insecticide on *Coptotermes formosanus* (Isoptera: Rhinotermitidae)," *Trop. Pest Manage.*, vol. 38, pp. 176-180 (1992); C. K. Wilkins, "Naturally occurring anti-termite compounds," *Mater. Org.*, vol. 27, pp. 47-66 (1992); and B. C. R. Zhu et. al., "Nootkatone is a repellent for Formosan subterranean termite (*Coptotermes formosanus*)," *J. Chem. Ecol.*, vol. 27, pp. 523-531 (2001).

Several natural chemicals that repel termites have been described. The mature leaves of two species of *Cinnamomum, C. osmophloeum* Kaneh. and *C. zeylanicum* B1, have been found to impart termite resistance. The main components ofthe oil extracted from these two species were cinnamic aldehyde and eugenol, with eugenol exhibiting greater resistance to termites. See Tien-shu Lin et al., "The effects of *Cinnamomum* spp. Oils on the control of termite *Coptotermes formosanus* Shiraki," Taiwan For. Res. Inst. New Series, vol. 10 pp.459-464 (1995). The woods of the Alaska-cedar, redwood, and teak were found to be resistant to Formosan subterranean termites. Although the termites fed on the wood, it was to a limited extent. See, e.g., J. K Grace, "Natural resistance of Alaska-cedar, redwood, and teak to Formosan subterranean termites," Forest Products Journal, vol. 44, pp.41-45 (1994). Vetiver oil and certain extracts of vetiver oil have been shown to be toxicants and repellents against termites. See, e.g., L. Maistrello et al., "Effects of nootkatone and a borate compound on Formosan subterranean termites (Isoptera: Rhinotermitidae) and its symbiont protozoa," *J. Entomol. Sci.*, vol.36, pp. 229-236 (2001); L. Maistrello et al., "Efficacyof vetiver oil and nootkatone as soil barriers against Formosan subterranean termite (Isoptera: Rhinotermitidae)," *J. Econ. Entomol.*, vol. 94, pp.1532-1537 (2001); and B. C. R, Zhu et al., "Nootkatone is a repellent for Formosan subterranean termite (*Coptotermes Formosanus*)," *J. Chem. Ecol.*, vol. 27, pp. 523-531 (2001); and B. C. R. Zhu et al., "Evaluation of vetiver oil and seven insect-active essential oils against Formosan subterranean termites," *J. Chem. Ecol.*, vol. 27, pp. 1617-1625 (2001).

The search for new repellents is difficult because termites have shown unexpected sensitivity and tolerance to certain chemicals, reactions that differ from that of other insects. For example, 2-phenoxyethanol has been shown to be a trail-following substance for termites; and naphthalene, which is known as a moth repellent and a toxicant for other insects, was found in termite nests at concentrations that are known to kill fire ants. See U.S. Pat. No. 5,874,097; J. Chen et. al., "Isolation and identification of 2-phenoxyethanol from ball-point pen as a trail-following substance of *Coptotermes formosanus* Shiraki and *Reticulitermes* spp.", J. Entomol. Sci., vol. 33, pp. 97-105 (1998); and J. Chen et al., "Termites fumigate their nests with naphthalene," Nature, vol. 392, pp. 558-559 (1998). Naphthalene is most commonly used as a moth repellent in the form of mothballs or crystals, and as a toilet deodorant block. See Agency for Toxic Substances and Disease Registry (ATSDR), Toxicological profile for naphthalene, 1-methylnaphthalene and 2-methylnaphthalene, Atlanta, Ga.: U.S. Dept. of Health and Human Services, Public Health Service (1995). It is also used in the synthesis of the insecticide, carbaryl, which is known for its low mammalian toxicity.

Several derivatives of naphthalene are known. FIG. 1 illustrates the structure of naphthalene and 10 of its derivatives.

U.S. Pat. No. 4,788,341 discloses a process for preparing 2'-acetonaphthone by using compounds selected from a group consisting of ketals and enol ethers of acetyl-substituted benzalacetone.

U.S. Pat. No. 4,107,066 discloses a process for preparing acetonaphthones and uses of the prepared compounds in perfumery.

We have discovered that several derivatives of naphthalene, including 1'-acetonaphthone, 2'-acetpnaphthalone, 1-methoxynaphthalene, and 2-methoxynaphthalene, are effective repellants and toxicants of termites. For example, 2'-acetonaphthone was found to be an effective repellent against termites. Termites exposed to concentrations as low as 8 mg/kg sand exhibited a significant reduction in tunneling and feeding activity. Moreover, some of the dead termnites had symptoms indicative of a failure to molt. At concentrations $\geq$20 µg/cm$^2$, 2'-acetonaphthone was a strong repellent. Interestingly, at 160-fold lower concentration (0.125 µg/cm$^2$), 2'-acetonaphthone stimulated termite feeding activity.

Figure 1:
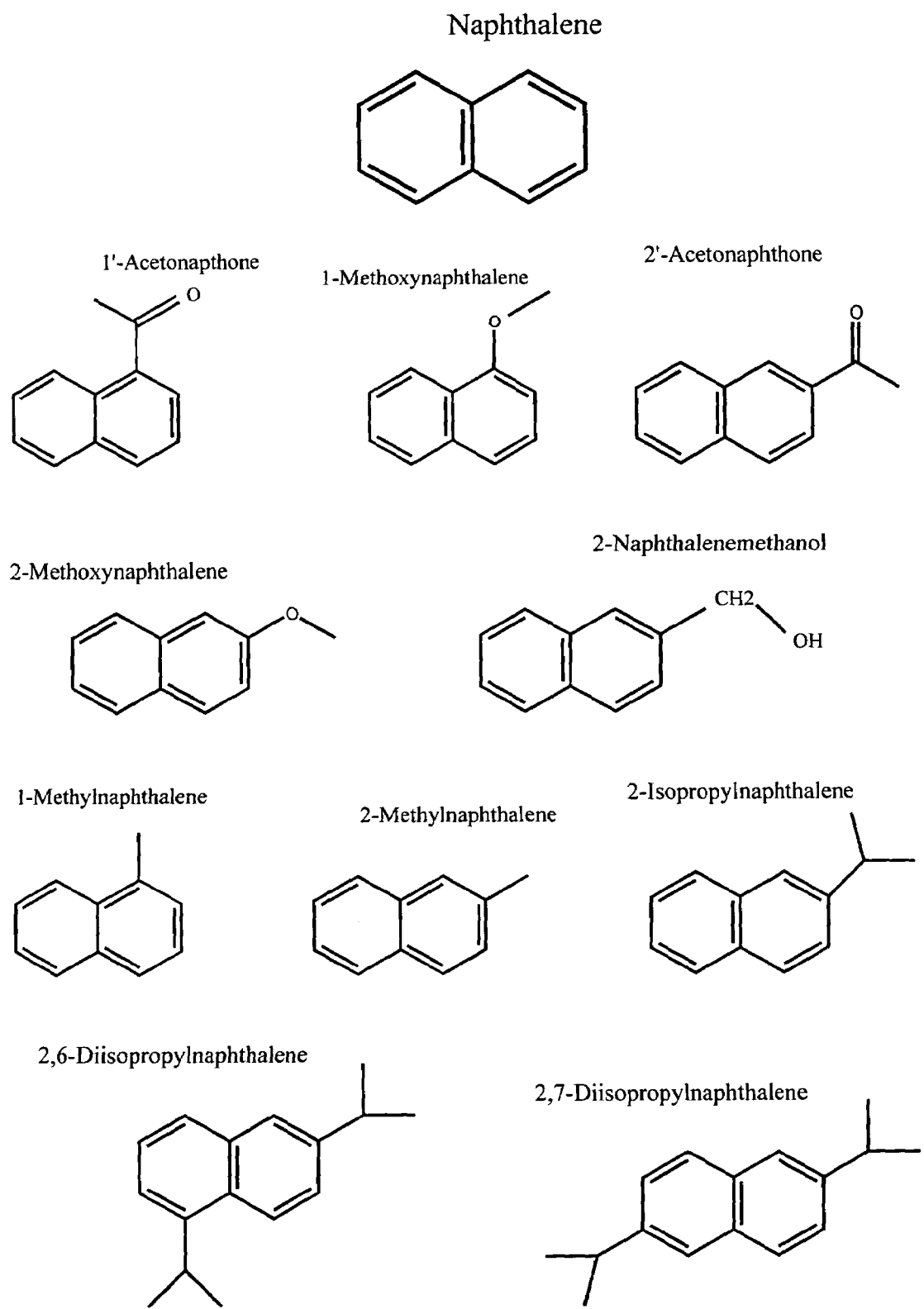
FIG. 1 illustrates the chemical structure of naphthalene and ten of its related compounds, including 1'-acetonaphthone, 2'-acetonaphthone, 1-methoxynaphthalene, and 2-methoxynaphthalene.

We have shown that certain derivatives of naphthalene, especially 1'-acetonaphthone, 2'-acetonaphthone, 1-methoxynaphthalene, and 2-methoxynaphthalene, repel termites and consequently result in a significant reduction in their feeding activity. Certain properties of 2'-acetonaphthone make this chemical attractive as a possible termite control agent: (1) 2'-acetonaphthone, as an alkyl derivative of naphthalene, is expected to be more persistent and safer to the environment than naphthalene due to its lower volatility and lower water solubility. See e.g., C. D. Knightes et al., "Substrate interactions in the biodegradation kinetics of polycyclic aromatic hydrocarbons (PAH) mixtures," Biotech. & Bioeng., vol. 69, pp. 160-170 (2000); (2) 2'-acetonaphthone is used as an ingredient of several fragrances, including soaps, detergents, beauty care and other household products; (3) it is considered by the Environmental Protection Agency (EPA) to be a non-hazardous air pollutant; and (4) it is relatively inexpensive.

The strong repellency of 2'-acetonaphthone at low concentrations allow for possible future use in an economical method to prevent termites, especially Formosan subterranean termites. Moreover, the water insolubility and low volatility of 2'-acetonaphthone may indicate a longer effective period after application.

EXAMPLE 1

Materials and Data Analysis

Source of the Termites

Five colonies were collected from different locations in Louisiana. Three colonies were from different locations in Lake Charles, La., Colonies C, E, and CR, collected in June 2001, April 2002, and May 2002, respectively. Two colonies were from two location in New Orleans, La. (Colonies BS and WB), and were collected in April 2002 and June 2002, respectively. After collection, the colonies were held separately in 250-liter cans at room temperature (26-28° C.) and 70-80% RH (relative humidity). The cans were surrounded with a metal water trough to prevent termite escape and ant invasion.

Source of Chemicals

Several derivatives of napthalene were assayed for termite acitivity. The following chemicals were purchased from Aldrich Chemical Co. (Milwaukee, Wis.): 98% crystal napthalene; 98% liquid 1'-acetonaphthone; 99% crystal 2'-acetonaphthone; 98% liquid 1-methoxynapththalene; 99% crystal 2-methoxynaphthalene; 98% crystal 2-naphthalene methanol; 95% liquid 1-methylnaphthalene; and 97% crystal 2-methylnaphthalene. Three derivatives were purchased from TCI America (Portland, Ore.): 95% liquid 2-isopropoylnaphthalene (beta-); 99% crystal 2,6-diisopropylnaphthalene; and 95% liquid 2,7-diisopropylnapthalene.

Data Analysis

Dose-mortality data were analyzed using probit analysis as adapted for PC use (POLO-PC), which automatically corrected for control mortality using Abbott's transformation. See, e.g., R. M Russell et al., "POLO: a new computer program for probit analysis," Bull. Entomol. Soc. Am., vol. 23, pp. 209-213 (1977); and LeOra Software, "POLO-PC, a user's guide to probit analysis or logit analysis" (1987). The $LD_{50}$s of workers and soldiers from four tested colonies (y) were plotted against the average weight of tested termites (x) to establish a linear regression equation and conduct correlation analyses. Mean survival, food consumption and tunnel areas were compared among treatments using analysis of variance (ANOVA), followed by least significant difference procedures. See, SAS Institute, SAS/STAT User's Guide: version 8, SAS Institute, Inc., Cary, N.C. (1999). In two-choice assays using either treated filter paper or treated sand, the parameters measured in the two lateral sides of each treatment were compared using paired t-tests. All data were judged at $\alpha=0.05$.

EXAMPLE 2

Topical Toxicity of 2'-Acetonaphthone

Acute toxicity of 2'-acetonaphthone was bioassayed using doses that ranged from 1.25 to 20 ug/termite. At stock solution of 2'-acetonaphthone was prepared (1 g/5 ml acetone). Dilutions were made by taking aliquots from the stock solution (62.5, 125, 250, 375, 500, 750, and 1000 µl), and adjusting each volume to 2 ml with acetone. A group of 20 workers or soldiers (from colonies BS, WB, E and CR) were placed in a Petri dish (6 cm×1.5 cm) and chilled on top of an ice brick (30.32 cm×17.78 cm×3.81 cm; IceBerg, Mid-Lands Chemical Company, Inc., Miami, Fla.) to slow their movement. Each termite was treated with a topical dose in 0.2 µl acetone to the dorsum of the mesothorax using a Hamilton PB 600 Repeating Dispenser equipped with a 10 µl syringe (Hamilton, Reno, Nev.). The experimental termites were treated with doses equivalent to 1.25, 2.50, 5.0, 7.5, 10.0, 15.0, and 20.0 µg/termite. Control termites were dosedwith only 0.2 µl acetone. Five replicates, each with 20 workers or 20 soldiers, were used for each dose and control. For each replicate, termites were maintained in a plastic container (5.5 cm×3.7 cm, Pioneer Pckaging Co., North Dixon, Ky.), each provided with a filter paper (Whatman #2, 55 mm diameter) wetted with 250 µl double distilled water ($DDH_2O$). The containers were covered with lids, and kept for 2 days at room temperature (26-28° C.). Daily mortality in each dish was recorded. Termites were considered dead if unable to right themselves when prodded with a fine paint brush.

Probit analysis results are shown in Table 1 below. The $LD_{50}$ and $LD_{90}$ values were calculated as described in Example 1. The 48 h-$LD_{90}$ ranged from 3.09 -11.77 µg/worker and 4.07-12.32 µg/soldier. A higher susceptibility to 2'-acetonaphthone was exhibited by workers from colonies BS and WB. Of the four tested colonies, workers form colony E were significantly more tolerant than those from WB and BS colonies (based on the non-overlap of 95% confidence limits of 24 h and 48 h data). However, the difference between colonies CR and E was only significant at 24 h. Soldiers from the four colonies responded to 2'-acetonaphthone in a similar manner based on toxicity data at 24 h. However, at 48 h, a lower susceptibility by soldiers from colony E was seen as compared to the other colonies (Table 1). The correlations between $LD_{50}$s and the average weight of treated termites were not significant (R=0.435, P=0.282 for 24 h $LD_{50}$ and R=0.5349, P=0.172 for 48 h $LD_{50}$; data not shown). Chi-square values of LOgit-dose-probit lines were significant for the soldiers from WB (Table 1). For each tested colony, soldiers and workers responded similarly with no significant differences between the toxicity parameters at 24 h and 48 h.

Although some differences between colonies were seen, termites from the four colonies exhibited a toxicity response to 2'-acetonaphthone at doses less than 13 µg/termite (dose that killed 90% termites).

TABLE 1

Probit analysis results of *C. formosanus* workers and soldiers exposed to 2'-acetonaphthone in topical application assays

| Colony | LD-P line value[a] | 24 hours | | 48 hours | |
|---|---|---|---|---|---|
| | | Worker | Soldier | Worker | Soldier |
| BS | $LD_{50}$ (95% CL)[b] | 2.21 (1.91-2.49) | 3.24 (2.27-4.24) | 1.74 (1.49-1.96) | 2.02 (1.49-2.46) |
| | $LD_{90}$ (95% CL) | 7.11 (6.14-8.58) | 13.60 (8.86-15.01) | 4.19 (3.73-4.83) | 4.07 (3.37-5.37) |
| | Slope ± SE | 2.52 ± 0.22 | 2.06 ± 0.20 | 3.35 ± 0.30 | 4.22 ± 0.40 |
| | $\chi^2$, df, P | 2.57, 4, 0.6321 | 5.86, 4, 0.2098 | 1.51, 4, 0.8249 | 7.28, 4, 0.1218 |
| WB | $LD_{50}$ (95% CL) | 1.75 (0.76-2.76) | 2.16 (0.56-6.23) | 1.71 (0.42-1.95) | 2.17 (0.49-5.76) |
| | $LD_{90}$ (95% CL) | 6.33 (3.71-12.46) | 5.48 (1.42-15.81) | 3.09 (2.70-3.72) | 5.59 (1.23-14.49) |
| | Slope ± SE | 2.29 ± 0.24 | 3.09 ± 0.27 | 4.99 ± 0.74 | 3.12 ± 0.49 |
| | $\chi^2$, df, P | 4.93, 4, 0.2946 | 19.34, 4, 0.0007[c] | 0.72, 4, 0.9488 | 13.96, 4, 0.0074[c] |
| CR | $LD_{50}$ (95% CL) | 2.93 (2.24-3.59) | 3.49 (2.49-4.51) | 2.67 (1.87-3.35) | 2.02 (1.48-2.48) |
| | $LD_{90}$ (95% CL) | 7.23 (5.59-11.34) | 8.09 (5.94-16.01) | 6.09 (4.85-8.82) | 4.26 (3.45-5.92) |
| | Slope ± SE | 3.27 ± 0.24 | 3.51 ± 0.26 | 3.57 ± 0.33 | 3.95 ± 0.33 |
| | $\chi^2$, df, P | 5.67, 4, 0.2252 | 7.38, 4, 0.1171 | 5.66, 4, 0.2260 | 6.56, 4, 0.1610 |
| E | $LD_{50}$ (95% CL) | 7.24 (5.22-9.36) | 5.12 (3.99-7.24) | 3.82 (2.68-5.83) | 4.19 (3.14-6.20) |
| | $LD_{90}$ (95% CL) | 19.69 (14.02-25.58) | 14.06 (9.51-19.26) | 11.77 (7.66-17.79) | 12.32 (8.23-15.32) |
| | Slope ± SE | 2.99 ± 0.20 | 2.93 ± 0.19 | 2.55 ± 0.19 | 2.79 ± 0.19 |
| | $\chi^2$, df, P | 6.52, 5, 0.1635 | 3.21, 5, 0.5233 | 8.99, 5, 0.1095 | 3.74, 5, 0.5874 |

[a]Number of termites on which each probit analysis is based was 700-800.
[b]Lethal doses are expressed as µg/termite.
[c]$\chi^2$ are significant, and express the non-fitness of mortality data on the logit dose-probit line.

EXAMPLE 3

2'-Acetonaphthone Added to Sole Termite Food Source

To assay the effect of 2'-acetonaphthone on termites when added to a sole food source, acute and cumulative toxicities of 2'-acetonaphthone-treated filter paper (Whatman #2) and balsa wood (*Ochroma lagopus* Swartz) slices (2.3 cm×4.0 cm) were evaluated. Seven concentrations (0, 1, 10, 50, 100, 500, and 1000 mg/l) were prepared in 100 ml ethanol. Six filter papers and six wood slices were soaked in each concentration for 4 h; control filter papers and wood slices were soaked only in ethanol. After treatment, the food sources were kept overnight at ambient conditions for solvent evaporation. Eighty-four plastic containers (5.5 cm diameter×3.7 cm height) were provided with 22 g of wetted sand (20 g sand (fine blasting sand #4, Cement Products Inc., Baton Rouge, La.) mixed with 2 ml $DDH_2O$). Then either a filter paper or a wood slice was separately placed to fit on the surface of the wetted sand and wetted with $DDH_2O$ (250 µl). Into each container, fifty workers and 20 soldiers were placed on the surface of the filter paper or wood slice. For each concentration and food sourse, three replicates received termites from colony C, and three replicates received termites from colony WB. The containers were covered and incubated for 10 days at 27.4° C. and 70% RH. Containers were monitored everytwo days to ensure suitable moisture. On days 1, 5 and 10, the number of living workers and soldiers were counted. An average percent survival was calculated for each treatment. (See Tables 2 and 3).

TABLE 2

Percent survival† of *C. formosanus* workers and soldiers exposed to 2'-acetonaphthone-treated filter paper as the sole food source.

| Concentration | Day 1 | | Day 5 | | Day 10 | |
|---|---|---|---|---|---|---|
| (mg/l) | Worker | Soldier | Worker | Soldier | Worker | Soldier |
| 0 | 85.33 ± 2.91 a | 72.50 ± 9.64 a | 61.0 ± 9.87 ab | 45.0 ± 13.61 a | 50.33 ± 10.83 a | 44.17 ± 13.07 a |
| 1 | 87.67 ± 5.83 a | 84.17 ± 9.26 a | 73.0 ± 8.24 a | 58.33 ± 10.14 a | 55.67 ± 8.98 a | 60.83 ± 13.07 a |
| 10 | 84.0 ± 4.95 a | 80.0 ± 9.49 a | 66.67 ± 9.71 ab | 56.67 ± 12.49 a | 53.67 ± 12.92 a | 50.0 ± 12.91 a |
| 50 | 80.33 ± 9.76 a | 72.50 ± 11.46 a | 68.33 ± 11.56 ab | 42.50 ± 9.56 a | 55.0 ± 12.07 a | 35.83 ± 8.41 a |
| 100 | 80.0 ± 6.68 a | 73.33 ± 5.87 a | 48.33 ± 10.33 b | 33.33 ± 11.53 a | 40.67 ± 9.98 a | 17.50 ± 5.74 b |
| 500 | 18.33 ± 6.60 b | 14.17 ± 5.23 b | 0.0 ± 0.0 c | 0.0 ± 0.0 b | 0.0 ± 0.0 b | 0.0 ± 0.0 c |
| 1000 | 6.67 ± 6.67 b | 1.67 ± 1.67 b | 0.0 ± 0.0 c | 0.0 ± 0.0 b | 0.0 ± 0.0 b | 0.0 ± 0.0 c |
| F; df | 28.9; 6, 35 | 17.4; 6, 35 | 14.3; 6, 35 | 6.3; 6, 35 | 16.3; 6, 35 | 7.5; 6, 35 |
| P | <0.0001 | <0.0001 | <0.0001 | <0.0001 | <0.0001 | <0.0001 |

†Combined data of colony C and colony WB are expressed as percentages (mean ± SE) of survivors.
Means within a column followed by the same letter are not significantly different (P > 0.05).

The level of toxicity varied depending on the type of food and the termite group (worker or soldier), but not between the tested colonies (Tables 2 and 3). Because termites from the two tested colonies exhibited a similar trend in response to 2'-acetonaphthone (F=1.37; df=1,124; P=0.1068), data for the two colonies were combined. For filter paper treatments, concentrations of 2'-acetonaphthone up to 50 mg/l did not significantly affect either worker or soldier survival within the 10 day exposure (Table 2). Both soldier and worker survival was significantly reduced after 24 h in 500 and 1000 mg/l treatments as compared to the control (Table 2). After 10 days, 100 mg/l of 2'-acetonaphthone significantly affected survival rates of soldiers but not workers.

For the experiments using wood slices, 2'-acetonaphthone concentrations (1 to 1000 mg/l) did not show any toxicity within the first 24 h (Table 3). At day 5, soldier survival was significantly reduced in treatments of 500 and 1000 mg/l 2'-acetonphthone. However, 1000 mg/l 2'-acetonaphthone was the only treatment that showed a significant reduction in worker survival at day 5. By day 10, all treatments indicated a decrease in percent survival as compared to the control; however, the difference from the control was significant only at 1000 mg/l for workers, and at 500 and 1000 mg/l for soldiers.

Thus when the sole termite food source was impregnated with 2'-acetonaphthone, the termites showed decreased survival at 1000 mg/l. The susceptibility for soldiers was greater than that for workers, and 2'-acetonaphthone added to filter paper was more effective as a toxicant than similar concentrations added to a wood slice.

TABLE 3

Percent survival† of *C. formosanus* workers and soldiers exposed to 2'-acetonaphthone-treated wood slices as sole food source

| Concentration | Day 1 | | Day 5 | | Day 10 | |
|---|---|---|---|---|---|---|
| (mg/l) | Worker | Soldier | Worker | Soldier | Worker | Soldier |
| 0 | 88.33 ± 2.38 a | 91.67 ± 2.11 a | 69.33 ± 8.46 a | 58.33 ± 10.06 a | 64.0 ± 7.99 a | 54.17 ± 10.45 a |
| 1 | 85.0 ± 5.29 a | 93.33 ± 1.67 a | 55.33 ± 12.87 a | 60.0 ± 13.54 a | 52.67 ± 12.55 a | 47.50 ± 11.61 a |
| 10 | 83.33 ± 5.03 a | 86.67 ± 4.41 a | 63.67 ± 11.13 a | 54.17 ± 11.14 a | 50.67 ± 8.79 a | 46.67 ± 12.36 a |
| 50 | 86.67 ± 5.26 a | 85.0 ± 5.0 a | 65.0 ± 13.51 a | 48.33 ± 10.38 a | 49.67 ± 10.23 a | 39.17 ± 8.41 a |
| 100 | 88.67 ± 3.33 a | 90.0 ± 2.89 a | 56.67 ± 12.15 a | 55.83 ± 11.94 a | 47.67 ± 10.97 a | 45.0 ± 9.58 a |
| 500 | 84.67 ± 2.41 a | 80.83 ± 10.44 a | 54.33 ± 8.01 a | 17.50 ± 7.61 b | 30.67 ± 9.18 a | 4.17 ± 2.38 b |
| 1000 | 86.67 ± 3.53 a | 84.17 ± 7.24 a | 13.0 ± 9.85 b | 2.50 ± 2.49 b | 5.67 ± 4.27 b | 0.0 ± 0.0 b |
| F; df | 0.23; 6, 35 | 0.63; 6, 35 | 3.81; 6, 35 | 7.10; 6, 35 | 5.60; 6, 35 | 9.50; 6, 35 |
| P | 0.960 | 0.7030 | 0.0050 | <0.0001 | <0.0001 | <0.0001 |

†Combined data of colony C and colony WB are expressed as percentages (mean ± SE) of survivors.
Means within a column followed by the same letter are not significantly different (P > 0.05).

EXAMPLE 4

Repellency of 2'-Acetonaphthone When an Untreated Food Source is Available

2'-Acetonaphthone was tested for its repellency and consequently its effect on food consumption when termites had a choice of treated and untreated foods. Thirty-five transparent plastic containers (17.7 cm×8.0 cm×4.0 cm), Pioneer Packaging Co., North Dixon, Ky.), each with three chambers (8.0 cm×5.75 cm×4.0 cm), were used. An opening (3.5 cm×0.3 cm) was made at the bottom of each of the two inner walls, connecting the three chambers and allowing termites to move between the chambers. For each container, filter papers (Whatman #2, 5.5 cm diameter) were placed in the two lateral side chambers. For each treatment, five replicates (five containers) were used; for each replicate, one side chamber was marked "treated" and the other side chamber marked "untreated."

A stock solution of 2'-acetonaphthone was prepared by dissolving 0.952 mg (AI) in 5 ml ethanol (190.4 mg/l). One-half of this solution was used to apply 500 μl to filter paper placed in the "treated" chamber to test the highest concentration of 2'-acetonaphthone, 4.0 μg/cm$^2$. The remaining volume, 2.5 ml, was diluted by adding an equal volume of ethanol. One-half of this new solution was used to add 500 μl to each of 5 filter papers in a "treated" chamber to achieve a concentration of 2.0 μg/cm². This dilution and application step was repeated four more times to make four additional concentrations equivalent to 1.0, 0.50, 0.250 and 0.125 μg/cm². Filter papers placed in the "untreated" chambers were left untreated. Five containers served as replicates for each tested concentration. Five containers served as controls, in which filter paper in the "treated" chamber received 500 μl ethanol, and that in the "untreated" chamber was left untreated.

Containers were kept at ambient conditons overnight for ethanol evaporation, and then all filter papers were weighed. In the middle chamber of all containers, 55 g wetted sand (50 g sand mixed with 5 ml $DDH_2O$) was added, then packed and leveled to allow for clear visualization of tunnels along the bottom of the containers. Treated and untreated filter papers were wetted with 250 μl $DDH_2O$. Then 100 workers and 5 soldiers from colony E were released onto the surface of the sand in the middle chamber.

The containers were covered and incubated for 12 days at 26.6° C. and 70% RH, and checked every 2 days for moisture content. The number of termites in the two lateral chambers was recorded daily for 3 days. On day 12, the bottom of each container was scanned (ScanJet 4c, Hewlett-Packard, Palo Alto, Calif.) and the images printed to measure and calculate the areas of tunnels. The experiment was ended on day 12, and the number of living termites in each container counted. The treated and untreated filter papers were gently cleaned using deionized water and a small brush to remove all debris. Filter papers were then oven dried at 60° C. for 3 h, and re-weighed to calculate food consumption.

A second trial was conducted with higher concentrations of 2'-acetonaphthone (5 to 40 μ/cm²) using the above technique with some modifications. A stock solution (1900 mg/l) was prepared by dissolving 0.038 g (AI) 2'-acetonaphthone in 20 ml ethanol. Dilutions were made by taking 6.0, 4.5, 3.0, 1.5, and 0.75 ml from the original stock, and adjusting the volume of each to 6.0 ml with ethanol to yield the following concentrations: 1900.0, 1425.0, 950.0, 475.0, 237.5 mg/l, respectively. For each concentration, ten containers were used, with the filter paper in the "treated" chamber coated with 500 μl of the tested concentration. Filter papers placed in the "untreated" chamber were left untreated. For controls, ten containers were similarly handled except that the filter paper in the "treated" chamber was coated with 500 μl ethanol. The solvent was allowed to evaporate overnight at ambient conditions. The final concentrations of 2'-acetonaphthone on the filter papers were 5, 10, 20, 30, and 40 μg/cm².

The ten containers for each concentration were equally divided into two equal sub-groups. In the first sub-group, all filter papers were wetted with 250 μl $DDH_2O$, and then 20 workers and 1 soldier from colony E were placed in the middle chamber of each container. The containers were covered with lids and with an opaque dark blue sheet to minimize the effect of the light. Five readings at 12 h intervals were made by counting the number of workers in "treated" and "untreated" chambers. After each reading, 50 μl $DDH_2O$ was added to each filter paper, and the containers were rotated 180° to minimize any effect of direction on termite orientation.

In the second sub-group, all filter papers were weighed and wetted with 250 μl $DDH_2O$, and then 100 workers and 5 soldiers from the same colony were placed in the middle chamber containing 55 g of wetted sand. This sub-group was incubated for 15 days at 26.6° C. and 70% RH, and checked every two days to provide moisture if needed. The number of termites in both side chambers was counted on day 8, and tunnels were scanned and measured as described above. On day 15, living termites were counted for each container. Treated and untreated filter papers were cleaned and dried as previously described, and food consumption was calculated.

Preliminary studies using only one concentration of 2'-acetonaphthone (23 μg/cm²) revealed that workers avoided the treated side, and that feeding activity after 8 days exposure was negligible. (data not shown)

Figure 2:
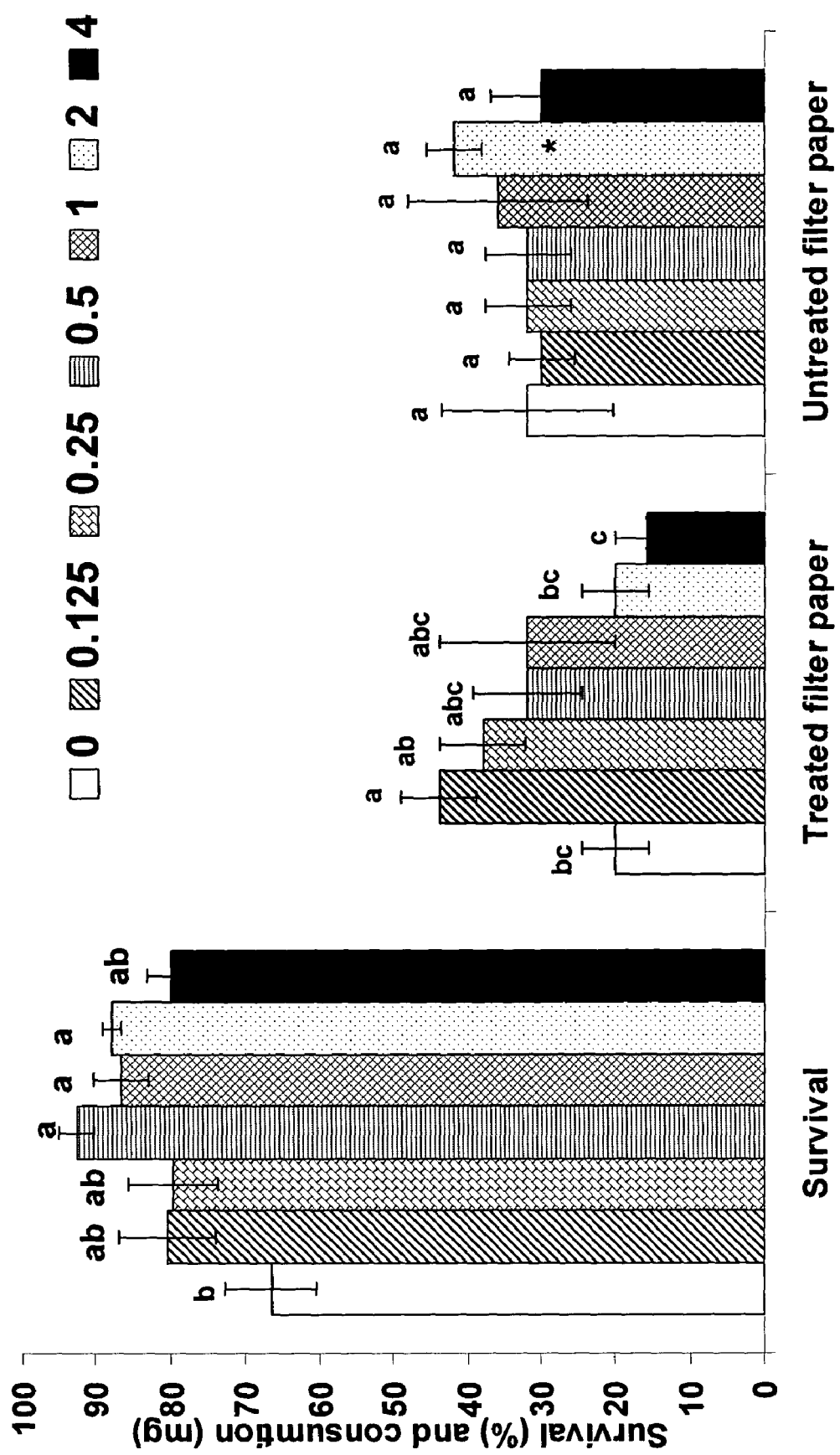
FIG. 2 illustrates the survival (mean percentage of survival (±SE)) as measured on day 12 and the food consumption (mean loss in weight (±SE) of treated and untreated filter paper) of C. formosanus workers during 12 days exposure to various concentrations (0.125 to 4.0 ug/cm$^2$) of 2'-acetonaphthone.

Another experiment was conducted using six concentrations of 2'-acetonaphthone (0.125 to 4 μg/cm²). The results are shown in FIG. 2. FIG. 2 illustrates the percent of *C. formosanus* survival and the weight (mean±SE) of treated and untreated filter paper during 12 days exposure. Within each group, bars marked by the same letters are not significantly different (P>0.05). The treatment bar with an asterisk (*) indicates a significant difference in filter paper consumption between untreated and treated chambers at that concentration, 2.0 μg/cm² (Paired t-test). The number of termites found in the treated side of all 2'-acetonaphthone treatments was not significantly different from the control (F=1.33; df=6, 28; P=0.2785; data not shown). Worker survival was greater in all chemical treatments compared to the controls. However, the differences with the control were significant only at 0.5, 1.0 and 2.0 μg/cm² concentrations (F=3.32; df=6, 28; P=0.0135).

As seen in FIG. 2, filter paper consumption measured on day 12 was higher in the treatments of 0.125 to 1 μg/cm², but this difference was significant from the control only in the 0.125 μg/cm² treatment (F=2.43; df=6, 28; P=0.0509; FIG. 2). Untreated filter paper consumption in all treatments including the control was not significantly different (F=0.3; df=6, 28; P=0.934; FIG. 2). Only at 2 μg/cm², was a significant difference between treated and untreated filter paper consumption found (t=−3.77; df=8; P=0.0054). With the exception of the highest treatment, 4 μg/cm², total food consumption in the treatments was greater than in the control, however the difference was not significant (F=1.83; df=6, 28; P=0.1295; data not shown). Tunnels areas measured on day 12 were not significantly different between the control and any 2'-acetonaphthone treatments (F=2.01; df=6, 28; P=0.0982; data not shown).

Thus at the lower concentrations (≦2 μg/cm²) of 2'-acetonaphthone, there is some evidence of increased feeding and increased worker survival. However, a significant feeding stimulation was found only at 0.125 μg/cm², a concentration 160-fold lower than an effective concentration for reduction in food consumption. At low concentrations, 2'-acetonaphthone could be used as a bait additive to stimulate feeding.

Figure 3:
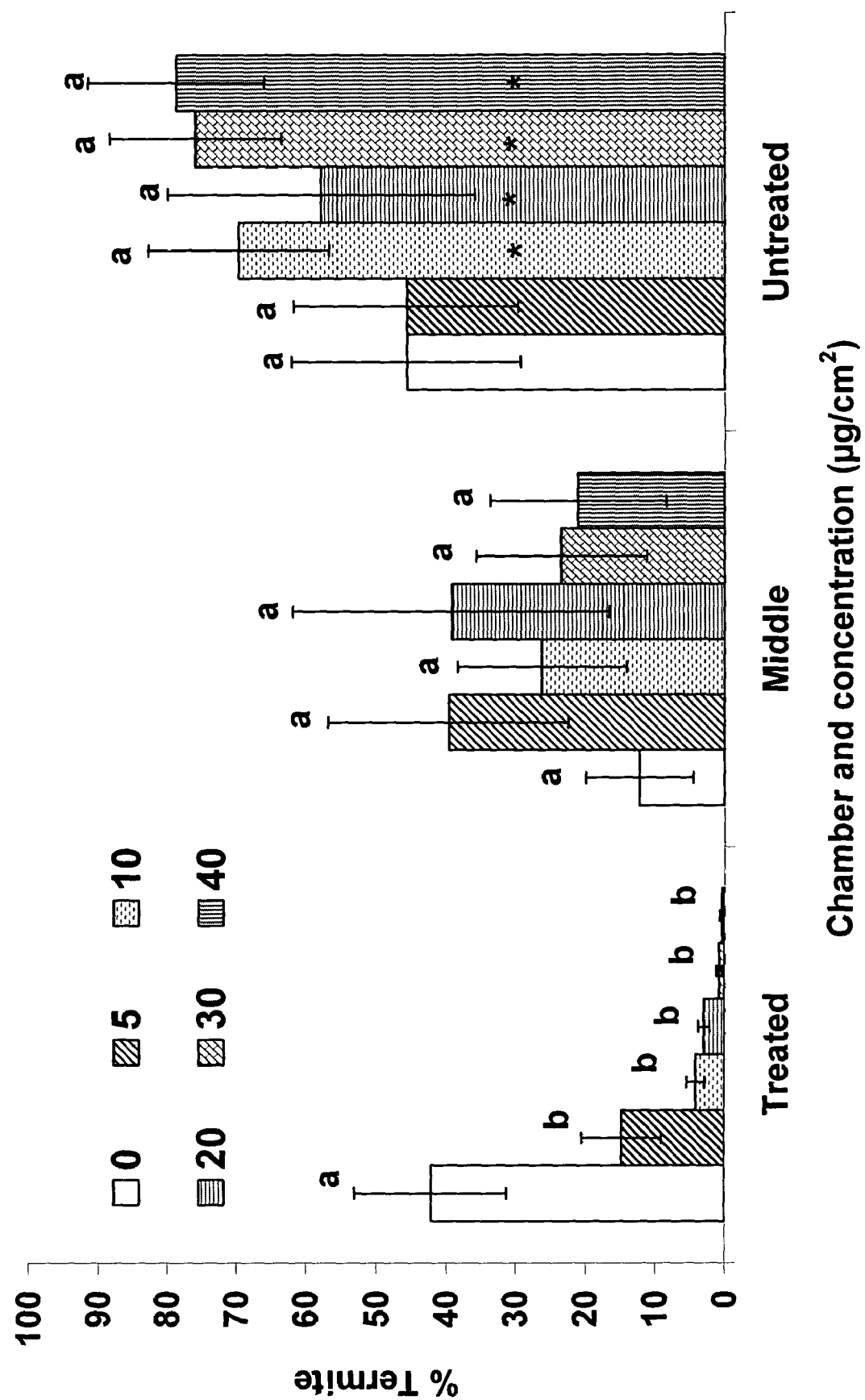
FIG. 3 illustrates the percentage (mean±SE of five readings at 12 h intervals) of C. formosanus workers counted in the three chambers (chamber with treated filter paper, middle chamber with no filter paper, and chamber with untreated filter paper), using various concentrations (5.0 to 40 ug/cm$^2$) of 2'-acetonaphthone for the treated chamber.

In another set of experiments, higher concentrations of 2'-acetonaphthone (5 to 40 μg/cm²) were used. At these concentrations, 2'-acetonaphthone was shown to be a repellant. Within the first 3 days, the number of termites in the treated chambers at all treatments was significantly lower than those in the ethanol-treated chamber of the control (F=10.26; df=5, 24; P<0.0001; FIG. 3). However, the percentage of termites in the middle chamber (F=0.52; df=5, 24; P=0.756) and in the untreated chamber (F=0.87; df=5, 24; P=0.519) remained similar at all treatments, including the control. FIG. 3 indicates the percent (mean±SE) *C. formosanus* workers counted (mean of five readings at 12 hr interval) in 2'-acetonaphthone "treated" and "untreated" filter paper chambers, and in the middle chamber. Bars within a group that are marked by the same letters are not significantly different (P>0.05). Treatment bars marked with an asterisk (*) indicate a significant difference in filter paper consumption between untreated and treated sides (Paired t-test; Table 4). Containers with ≧10.0 μg/cm² 2'-acetonaphthone had significantly more termites in the untreated chamber than in the treated chamber (FIG. 3 and Table 4 below).

Figure 4:
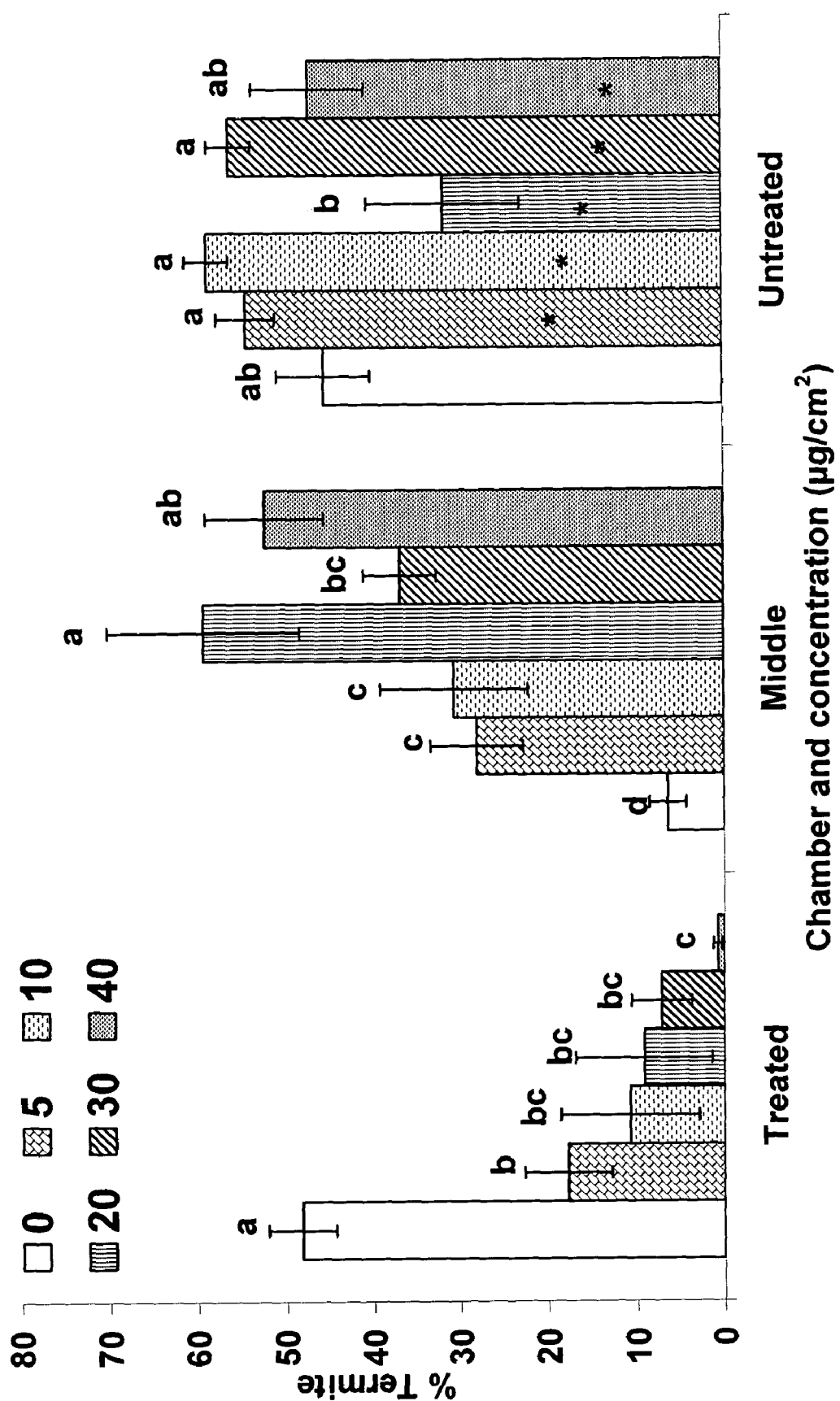
FIG. 4 illustrates the percentage (mean±SE) of C. formosanus workers on day 8 in three chambers (chamber with treated filter paper, middle chamber with no filter paper, and chamber with untreated filter paper), using various concentrations (5.0 to 40 ug/cm$^2$) of 2'-acetonaphthone for the treated chamber.

By day 8, the percent termites in the "treated" chamber of all 2'-acetonaphthone treatments was significantly lower compared to the ethanol "treated" chamber of the control (F=9.96; df=5, 24; P<0.0001; FIG. 4). Significant differences in termite distribution were observed between the chambers in containers with ≧5.0 μg/cm² 2'-acetonaphthalone (paired t-test; FIG. 4, and Table 4). FIG. 4 indicates the percent termite workers (mean±SE) on day 8 in 2'-acetonaphthone-treated and -untreated filter paper chambers, and in the middle chamber. Within each group, bars marked by the same letters are not significantly different (p>0.05). For each concentration, bars marked with an asterisk (*) indicate significant differences in termite distribution between the "treated" and "untreated" chambers. (See Table 4). Termite numbers in the middle chamber in all 2'-acetonaphthone treatments were significantly greater than in the middle chamber of the control (F=7.44; df=5, 24; P=0.0002; FIG. 4). Survival rates after 15 days exposure for concentrations ≧20 μg/cm² were reduced (45.0-51.2%) compared to the control (63.0%), but the difference was not significant (F=2.46; df=5, 24; P=0.0621; data not shown).

Figure 5:
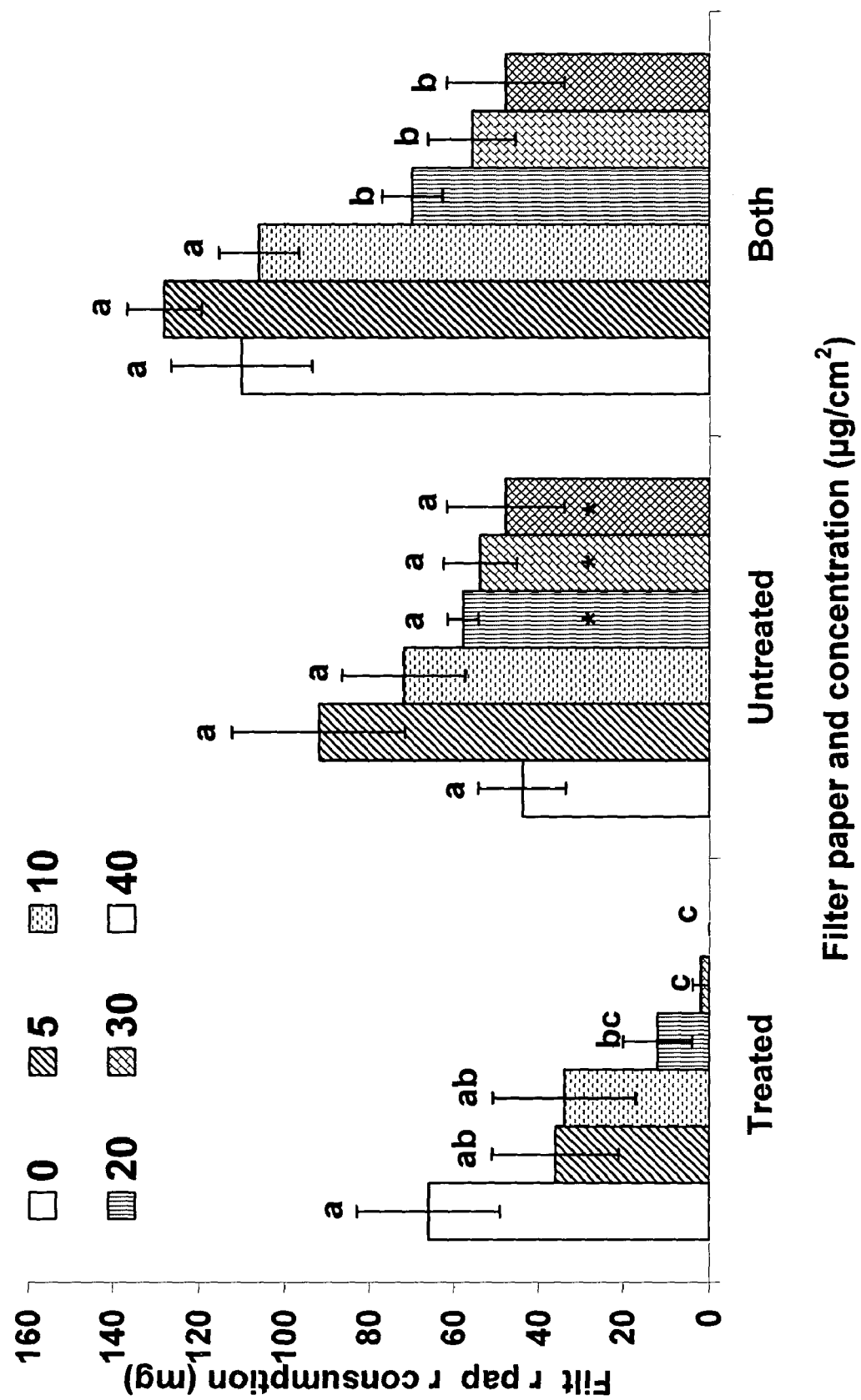
FIG. 5 illustrates the food consumption by C. formosanus workers (measured by loss in filter paper weight, mean±SE) of 2'-acetonaphthone-treated (at various concentrations, 5.0 to 40 ug/cm$^2$) and untreated filter papers after 15 day exposure.

As compared to the controls, 2'-aceetonaphthone at concentrations ≧20.0 μg/cm² was shown to be a significant repellent and consequently resulted in a significant reduction in the consumption of treated filter paper (F=4.44; df=5, 24; P=0.0053; FIG. 5), and in total consumption of treated and untreated filter paper (F=4.44; df=5, 24; P=0.0053; FIG. 5). FIG. 5 indicates the weight (mean±SE) of 2'-acetonaphthone treated filter papers, untreated filter paper, and both consumed by *C. formosanus* workers after 15 days exposure. For each group, bars in FIG. 5 marked by the same letter are not significantly different (P>0.05). Treatment bars marked with an asterisk (*) indicate significant differences in filter paper consumption between untreated and treated sides (Paired t-test; Table 4). Untreated filter paper consumption in all 2'-acetonaphthone treatments was not significantly different from the control (F=1.88; df=5, 24; P=0.1349; FIG. 5). Total food consumption on treated and untreated filter papers was significantly reduced in concentrations ≧20.0 μg/cm² compared to the control, and to the lower tested concentrations (F=8.21; df=5, 24; P=0.0001; FIG. 5). Significant differences in the consumption of treated and untreated filter paper were found in treatments with concentrations ≧20.0 μg/cm² (Paired t-tests, Table 4). Consumption of untreated filter paper in all 2'-acetonaphthone treatments was not significantly different from that of the control. (F=1.88; df=5, 24; P=0.1349; FIG. 5).

TABLE 4

Paired t-test results for *C. formosanus* distribution and food consumption when exposed to 2'-acetonaphthone at different concentrations.

| Treatment (μg/cm²) | Termite distribution[a] within the first three days | Termite distribution[c] on day 8 | Feeding activity[d] |
|---|---|---|---|
| 0 | 0.17; 0.8679[b] | 0.43; 0.6789 | 1.11; 0.2988 |
| 5 | 1.80; 0.1095 | −6.24; 0.0002 | −2.21; 0.0578 |
| 10 | 5.01; 0.0010 | −5.82; 0.0004 | −1.70; 0.1277 |
| 20 | 2.49; 0.0375 | −1.91; 0.00922 | −5.21; 0.0008 |
| 30 | 6.02; 0.0003 | −11.46; <0.0001 | −5.81; 0.0004 |
| 40 | 6.18; 0.0003 | −7.26; <0.0001 | −3.45; 0.0087 |

[a]The results are for termite distribution between the two side chambers. (FIG. 3)
[b]The t value and P-values are given; df are 4 for all comparisons.
[c]The results are for termite distribution between the two side chambers. (FIG. 4)
[d]The results are for food consumption on treated and untreated filter paper after 15 days exposure. (FIG. 5)

2'-Acetonaphthone was a strong repellent and consequently resulted in a significant reduction in feeding activity at concentrations ≧20.0 μg/cm² when the termites had an alternative food choice. However, as shown above, at 160-fold lower concentration, 2'-acetonaphthone acts as a feeding stimulant. The toxicity was greater when the termites were not given a choice of food. However, in the food choice experiments, 2'-acetonaphthone was more repellent than toxic. The chemical is semi-volatile and thus able to repel termites outside the treated area.

EXAMPLE 5

2'-Acetonaphthone as a Barrier to Termite Movement

Three-chambered transparent plastic containers as described in Example 4 were used to test the effectiveness of 2'-acetonaphthone as a barrier to prevent termites from reaching a food source. Each tested concentration of 2'-acetonaphthone was dissolved in 60 ml ethanol and mixed with 600 g of sand. For a control, 600 g of sand was mixed with 60 ml ethanol. The untreated and treated sand were placed in holding containers, and kept overnight at ambient conditions for solvent evaporation. In each container, sand was mixed with 60 ml $DDH_2O$. Into the middle chamber, 110 g of either treated or untreated sand was gently added, packed, and leveled to clearly see tunnels. Six replicates were used for each concentration and control. Weighed balsa wood slices (0.159 cm×3.5 cm×6.0 cm, *Ochroma lagopus* Swartz) were placed in one of the two lateral chambers and wetted with 1 ml $DDH_2O$. Into each container, 200 workers and 20 soldiers were released in the opposite lateral chamber from the wood slice. Termites were thus required to cross through the treated sand in the middle chamber to reach the food source. Containers were covered, and incubated in complete darkness at 27.4° C. and 70% RH. If necessary, 1 ml $DDH_2O$ was added to the sand and wood slice twice a week to maintain proper moisture. Three separate experiments were conducted using the same technique with different colonies.

In the first experiment, termites from Colony BS were used, and tested concentrations of 2'-acetonaphthone were 0.0, 16.67, 33.33, 50.0, 100.0, and 200.0 mg/kg sand. The number of dead workers was recorded daily to day 6. On day 6, the number of living workers in the releasing chamber was also recorded, and the bottoms of the three-chambered containers were scanned (ScanJet 4C, Hewlett-Packard, Palo Alto, Calif.). The images were printed in actual size, and the tunnel areas measured. After 8 days, the total number of living workers in each container was recorded; and the wood slices were gently cleaned using deionized water with a small brush. The slices were then oven dried at 60° C. for 3 h and reweighed. The difference in weight of the wood slices from the initial weighing was used to calculate food consumption.

The second experiment was conducted as above with the following changes: (1) the concentrations of 2'-acetonaphthone were 4.16, 8.33, 16.67 and 33.33 mg/kg sand; (2) termites from a different colony (E) were used; (3) the number of termites in the releasing chamber (including both dead and living workers) was recorded on day 5; (4) cumulative worker mortality and the number of workers showing molting failures were recorded at days 1, 2, 5 and 7; and (5) tunnel areas, percent survival, and food consumption were measured on day 12.

The experiment was repeated a third time to further test for molting failures. The protocol was described as above. Five concentrations of 2'-acetonaphthone (4.15, 8.33, 16.67, 33.33, and 66.67 mg/kg sand) were evaluated using termites from colony WB. Tunnels were scanned, printed, and areas measured on days 2, 3, 4 and 7. Percent survival and food consumption were calculated on day 12 as previously described. To evaluate the effect of 2'-acetonaphthone treatments on worker survival, tunnel area and food consumption, an analysis of variance was conducted followed by a least significant difference procedure.

The results of the first experiment using 2'-acetonaphthone concentrations from 16.67 to 200 mg/kg are given in Table 5. On day 3, with the exception of one treatment (33.33 mg/kg), cumulative mortality was significantly higher in the containers with 2'-acetonaphthone than in controls. By day 6, cumulative mortality in all 2'-acetonaphthone treatments were significantly different from the controls, and had increased from day 3. No termites were observed in the releasing chamber of the control containers on day 6 compared to 39.8 to 81.8% in the releasing chamber of all containers with 2'-acetonaphthone. Concentrations of 100 and 200 mg/kg had the highest number of termites failing to cross the treated sand to reach the feeding chamber.

All 2'-acetonaphthone treatments significantly reduced tunneling activity and survival compared to the control (Table 5). Food consumption was significantly greater in control treatments, 98.3 mg, compared to $\leq 11.7$ mg in 2'-acetonaphthone treatments (Table 5). No food was consumed in the treatments having 2'-acetonaphthone at concentrations $\geq 50$ mg/kg.

In the second experiment, the protocol was similar but used lower concentrations of 2'-acetonaphthone and termites from colony E. These results are represented in Table 6. By day 5, most of the termites in the control containers had crossed the untreated sand barrier into the feeding chambers. (Table 6). However, in the containers with 2'-acetonaphthone-treated sand (4.16 to 33.33 mg/kg sand) in the middle chamber, significantly higher percentages (35 to 85%) of termites were found in the releasing chambers, indicating a reluctance to cross the treated sand to get to the feeding chamber. Moreover, at concentrations >8.16 mg/kg, no termite reached the feeding chamber. After 7 days, the containers with 2'-acetonaphthone-treated sand showed a significant increase in worker cumulative mortality compared to the control (Table 6). Moreover, in the containers with $\geq 8.33$ mg/kg 2'-acetonaphthone-treated sand, 70 to 100% of workers were found dead in the releasing chamber, and were rarely found on the surface of the treated sand. Although the lowest tested concentration (4.16 mg/kg) of 2'-acetonaphthone resulted in the lowest mortality percentage, the highest rate of malformed workers was found at this concentration (Table 6). By day 12, no significant differences were found between the treatments from 8.33 to 33.33 mg/kg in tunneling, feeding and survival, and all were significantly lower than the control. Food consumption at 4.16 mg/kg was significantly less than the control, but significantly greater than the higher concentrations of 2'-acetonaphthone.

TABLE 5

Orientation, percent survival, tunneling and feeding activities of *C. formosanus* workers exposed to 2'-acetonaphthone-treated sand.

| Concentration (mg/kg sand) | Termite* (%) day 6 | Mortality (%) day 3 | Mortality (%) day 6 | Tunnel area (cm$^2$) day 6 | Survival (%) day 8 | Consumption (mg) day 8 |
|---|---|---|---|---|---|---|
| 0.0 | 0 c† | 0 d | 0 c | 50.0 ± 6.1 a | 87.5 ± 1.6 a | 98.3 ± 15.6 a |
| 16.67 | 39.8 ± 8.8 b | 41.1 ± 11.2 ab | 74.2 ± 10.0 ab | 1.4 ± 0.9 b | 6.8 ± 6.7 b | 3.3 ± 3.3 b |
| 33.33 | 39.8 ± 10.2 b | 15.2 ± 6.1 cd | 54.8 ± 10.6 b | 5.5 ± 2.1 b | 19.1 ± 9.1 b | 11.7 ± 8.2 b |
| 50.0 | 31.2 ± 2.8 b | 57.6 ± 11.9 a | 89.8 ± 10.2 a | 2.5 ± 1.1 b | 1.8 ± 1.8 b | 0.0 ± 0.0 b |
| 100.0 | 79.8 ± 8.7 a | 31.8 ± 11.9 bc | 90.3 ± 5.1 a | 3.3 ± 1.6 b | 0.0 ± 0.0 b | 0.0 ± 0.0 b |
| 200.0 | 81.8 ± 6.0 a | 42.1 ± 5.6 ab | 94.8 ± 5.2 a | 0.0 ± 0.0 b | 1.3 ± 1.3 b | 0.0 ± 0.0 b |
| F | 19.2 | 5.4 | 21.2 | 49.5 | 51.4 | 28.3 |
| df | 5, 30 | 5, 30 | 5, 30 | 5, 30 | 5, 30 | 5, 30 |
| P | <0.0001 | 0.0012 | <0.0001 | <0.0001 | <0.0001 | <0.0001 |

*Percent workers (colony BS) in the releasing chambers.
†Data are expressed as mean ± SE.
Means within a column followed by the same letter are not significantly different (P > 0.05).

TABLE 6

Orientation, percent survival, tunneling and feeding activities of *C. formosanus* workers exposed to 2'-acetonaphthone-treated sand

| Treatment (mg kg$^{-1}$) | Termite (%)* | Mortality (%), day 7 | Molting failure (%), day 7 | Tunnel area (cm$^2$), day 12 | Survival (%), day 12 | Food consumption (mg), day 12 |
|---|---|---|---|---|---|---|
| 0.0 | 0.4 ± 0.2 c† | 7.0 ± 1.2 d | 0.0 ± 0.0 c | 32.5 ± 1.6 a | 66.0 ± 2.9 a | 108.3 ± 22.3 a |
| 4.16 | 34.9 ± 2.8 b | 35.9 ± 4.4 c | 26.7 ± 6.0 a | 22.8 ± 4.4 a | 34.2 ± 6.0 a | 27.1 ± 2.3 b |
| 8.33 | 77.9 ± 4.5 a | 71.8 ± 8.8 b | 11.5 ± 1.9 b | 2.8 ± 1.9 b | 4.2 ± 1.9 b | 0.0 ± 0.0 c |
| 16.67 | 78.6 ± 4.0 a | 99.5 ± 0.5 a | 13.9 ± 1.2 b | 0.0 ± 0.0 b | 0.0 ± 0.0 b | 0.0 ± 0.0 c |
| 33.33 | 79.6 ± 2.2 a | 100.0 ± 0.0 a | 15.9 ± 2.4 b | 0.0 ± 0.0 b | 0.0 ± 0.0 b | 0.0 ± 0.0 c |
| F | 81.3 | 101.8 | 9.7 | 165.7 | 336.8 | 23.7 |
| df | 4, 25 | 4, 25 | 4, 25 | 4, 25 | 4, 25 | 4, 25 |
| P | <0.0001 | <0.0001 | <0.0001 | <0.0001 | <0.0001 | <0.0001 |

*Percentages of workers (colony E) counted in the releasing chambers on day 5.
†Data are expressed as means ± SE.
Means within a column followed by the same letter are not significantly different (P > 0.05)

In the third experiment, the tunnel areas measured on day 2 were not significantly different between the control and any of the 2'-acetonaphthone treatments (Table 7). However, the construction of tunnels measured on days 3, 4, and 7 were significantly less at 2'-acetonaphthone$\geq$8.33 mg/kg as compared to that of controls. Survival and food consumption measured on day 12 were significantly reduced compared to the control in 2'-acetonaphthone concentrations $\geq$8.33 mg/kg.

The above experiment was repeated with new concentrations of 2'-acetonaphthone: 8.75, 17.5, 35, 70 and 140 mg/kg sand. Termites from colony E were tested, and the food source was changed to filter paper. Tunnels were scanned and measured on days 2, 5, 8 and 12. The data were analyzed as described in Example 5, and paired t-tests were used to compare tunneling and feeding activities between treated and untreated sides.

TABLE 7

Tunneling, feeding activities and survival of C. formosanus workers (colony WB) exposed to 2'-acetonaphthone-treated sand.

| Treatment (mg/kg) | Tunnel area (cm$^2$), day 2 | Tunnel area (cm$^2$), day 3 | Tunnel area (cm$^2$), day 4 | Tunnel area (cm$^2$), day 7 | Survival (%) day 12 | Food consumption (mg) day 12 |
|---|---|---|---|---|---|---|
| 0.0 | 4.6 ± 3.0 a† | 10.5 ± 3.4 a | 12.0 ± 3.2 a | 13.8 ± 3.8 a | 66.8 ± 5.7 a | 53.3 ± 10.2 a |
| 4.16 | 3.4 ± 1.6 a | 6.1 ± 2.6 ab | 8.0 ± 2.7 ab | 17.0 ± 4.5 a | 55.8 ± 7.3 a | 35.0 ± 13.8 a |
| 8.33 | 2.3 ± 1.3 a | 3.1 ± 1.2 bc | 3.5 ± 1.3 bc | 4.5 ± 1.8 b | 7.4 ± 3.3 b | 8.3 ± 3.1 b |
| 16.67 | 0.9 ± 0.4 a | 1.6 ± 1.0 bc | 1.7 ± 1.0 c | 0.7 ± 0.5 b | 0.0 ± 0.0 b | 3.3 ± 2.1 b |
| 33.33 | 0.0 ± 0.0 a | 0.0 ± 0.0 c | 0.0 ± 0.0 c | 0.0 ± 0.0 b | 0.1 ± 0.1 b | 3.3 ± 2.1 b |
| 66.67 | 0.4 ± 0.2 a | 0.4 ± 0.2 c | 0.4 ± 0.2 c | 0.4 ± 0.2 b | 0.0 ± 0.0 b | 4.2 ± 3.3 b |
| F; df | 1.5; 5, 30 | 4.7; 5, 30 | 6.7; 5, 30 | 8.8; 5, 30 | 55.9; 5, 30 | 8.3; 5, 30 |
| P | 0.2290 | 0.0027 | 0.0003 | <0.0001 | <0.0001 | <0.0001 |

†Data expressed as mean ± SE.
Means within a column followed by the same letters are not significantly different (P > 0.05).

Thus 2'-acetonaphthone formed an effective barrier against termites, at concentrations $\geq$8.33 mg/kg. At this concentration, 2'-acetonaphthone was both toxic and inhibited tunneling and feeding activities. The effective concentration of 2'-acetonaphthone is much lower and requires a shorter exposure time than other chemicals evaluated against the same species, C. formosanus. See, J. K. Grace et al., "Behavioral effects of a neem insecticide on Coptotermes formosanus (Isoptera: Rhinotermitidae)," Trop. Pest Management, vol. 38, pp. 176-180 (1992); and B. C. R. Zhu et al., "Nootkatone is a repellent for Formosan subterranean termite (Coptotermes formosanus)," J. Chem. Ecol., vol. 27, pp. 523-531 (2001).

EXPERIMENT 6

Effect of 2'-Acetonaphthone-Treated Sand When Untreated Sand is an Alternative

To further test the repellency of 2'-acetonaphthone, the three-chambered transparent plastic containers described in Example 5 were used. Sand was treated, allowed to dry from the solvent, and wetted with DDH$_2$O as described in Example 5. Treated sand was placed in one of the side chambers, and the other side chamber received an equal amount of untreated sand. The concentrations of 2'-acetonaphthone used were 4.16, 8.33, 16.67, 33.33 and 66.67 mg/kg sand. Each concentration and the control had five replicate containers. Weighed balsa wood slices (0.159 cm×3.5 cm×6.0 cm each) were placed on the surface of both treated and untreated sand, and were wetted with 1 ml of DDH$_2$O. Termites (200 workers and 20 soldiers) from colony WB were released in the middle chamber. On days 2, 3, 4 and 7, the bottom of each container was scanned, and tunnel areas measured as above. On day 12, the number of living termites in each container was recorded. The wood slices were then cleaned, dried and re-weighed to calculate food consumption.

Figure 6:
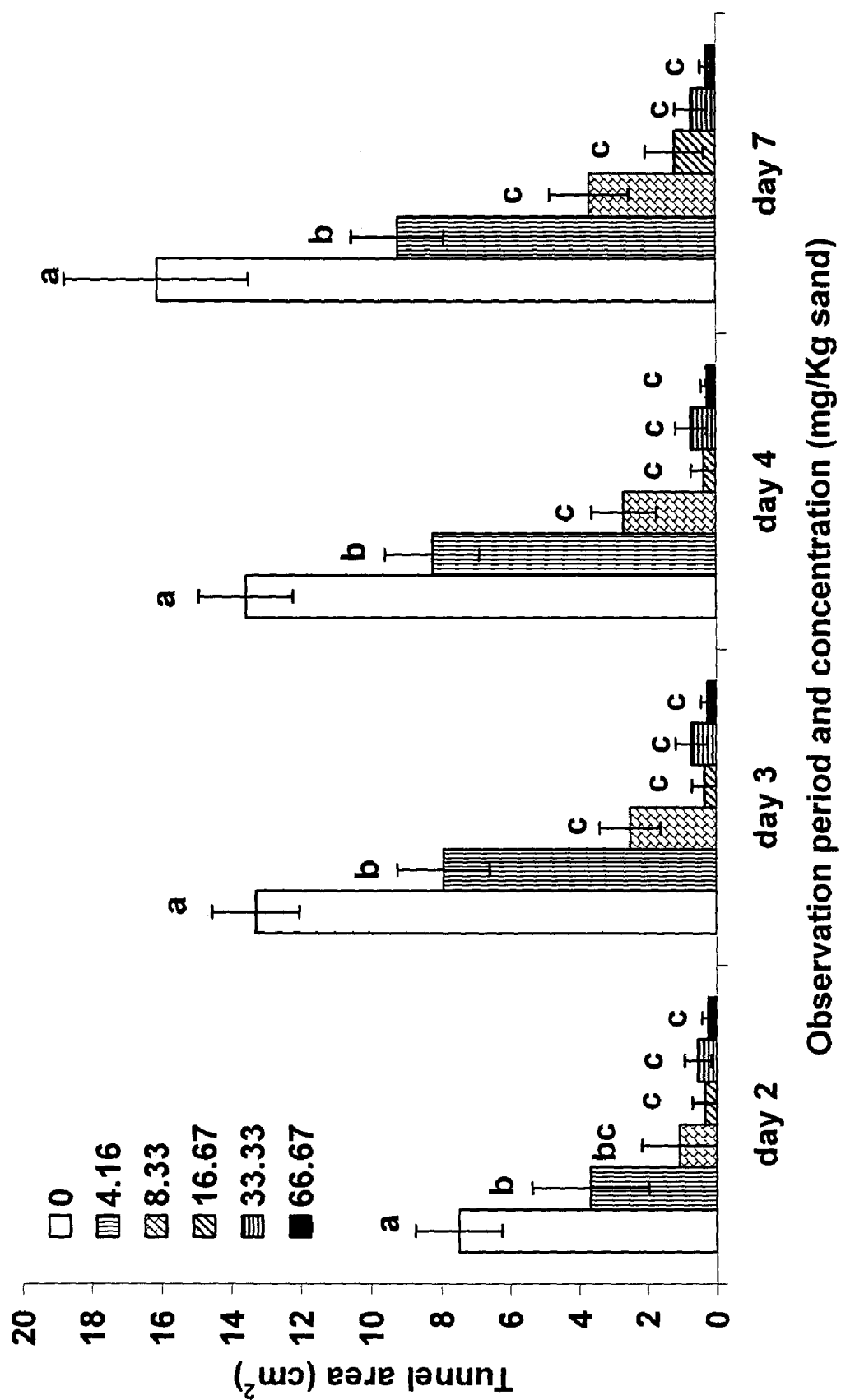
FIG. 6 illustrates the mean tunnel areas (±SE) constructed by C. formosanus workers in sand treated with various concentrations of 2'-acetonaphthone (from 0 to 66.67 mg/kg sand) as measured on days 2, 3, 4 and 7.
Figure 7:
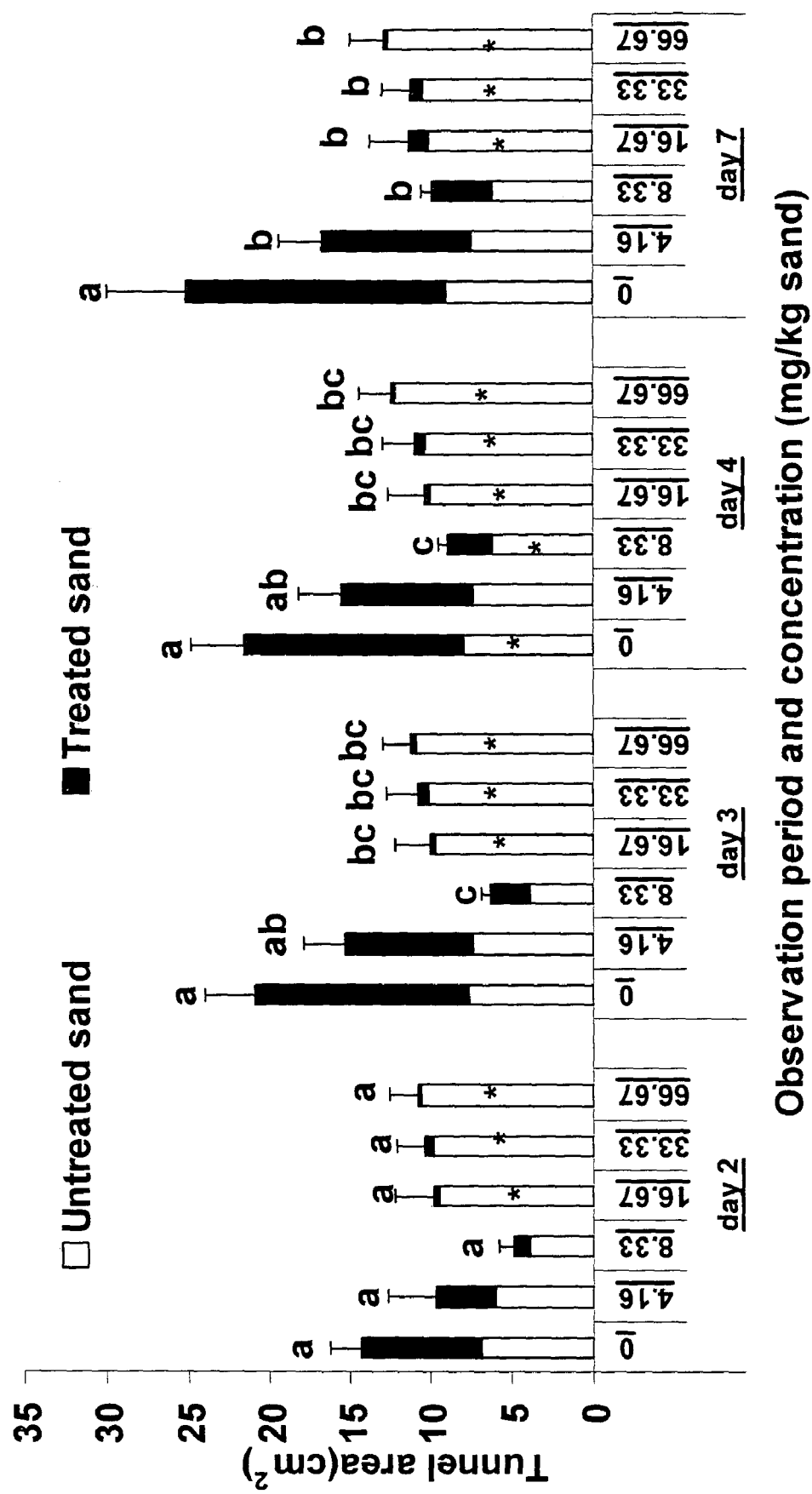
FIG. 7 illustrates the mean tunnel areas (±SE) constructed by C. formosanus workers in both 2'-acetonaphthone-treated (at various concentrations, 4.16 to 66.67 mg/kg sand) and untreated sand as measured on days 2, 3, 4, and 7.

In the first experiment, tunnel areas measured on days 2, 3, 4 and 7 indicated that termites constructed significantly shorter tunnels in the treated sand of all 2'-acetonaphthone treatments. (FIG. 6). FIG. 6 indicates the tunnel areas (mean±SE) constructed by C. formosanus workers (colony WB) in 2'-acetonaphthone-treated sand (4.16 to 66.66 mg/kg). For each observational period, bars marked by the same letter are not significantly different (F values are 8.44, 37.61, 36.56, and 21.55 for days 2, 3, 4, and 7, respectively; P<0.0001; and df are 5, 30 for all treatments). In contrast, tunnels constructed in untreated sand in all 2'-acetonaphthone treatments at all observation periods were not significantly different from the corresponding side of control treatment (where sand was left untreated; however, the opposite side was treated with ethanol). (F, P were 2.21, 0.0795 (day 2); 2.11, 0.0912 (day 3); 1.48, 0.2243 (day 4); 1.46, 0.2308 (day 7); df=5, 30 for all; FIG. 7). FIG. 7 indicates the dynamic changes in tunnel areas (mean±SE) constructed by C. formosanus workers (colony WB) in 2'-acetonaphthone-treated and untreated sand. Error bars and letters represent total tunneling activity measured in both treated and untreated chambers. For each observational period, bars marked by different letters are significantly different (F, P-values are 21.19, 0.01812 (day 2); 5.38, 0.0012 (day 3); 4.81, 0.0024 (day 4); 4.59, 0.0032 (day 7); df-values are 5,30 for all). For each treatment, bars marked with an asterisk (*) indicate a significant difference in tunneling activity between treated and untreated sand (paired t-tests; Table 8). For 2'-acetonaphthone treatments at $\geq$16.67 mg/kg sand, a significant difference was found in tunneling activity between untreated and treated sand chambers at the four periods of observation (paired t-tests, Table 8). With the exception of the lowest tested concentration and the first observation period, the sum of tunnels constructed in the 2'-acetonaphthone-treated (at $\geq$16.67 mg/kg) and untreated sand were significantly shorter than in the control (FIG. 7).

TABLE 8

Paired t-test results for comparing tunneling and feeding activities, and survival of *C. formosanus* workers (Colony WB) exposed to 2'-acetonaphthone-treated and untreated sand

| Treatment (mg/kg) | t-test values† for tunnel area (cm$^2$) and food consumption (mg) | | | | | Survival (mean % ± SE)‡ |
|---|---|---|---|---|---|---|
| | Tunnel area, day 2 | Tunnel area, day 3 | Tunnel area, day 4 | Tunnel area, day 7 | Food Consumption, day 12 | day 12 |
| 0.0 | 0.30 (0.7702) | 2.47 (0.0329) | 2.30 (0.0480) | 1.99 (0.0750) | 0.20 (0.8455) | 56.75 ± 4.46 a |
| 4.16 | −0.90 (0.3880) | 0.22 (0.8290) | 0.34 (0.7380) | 0.71 (0.490) | 0 (1.0) | 48.75 ± 2.78 ab |
| 8.33 | −1.95 (0.0795) | −1.04 (0.3210) | −2.39 (0.0380) | −1.57 (0.1480) | −2.07 (0.0653) | 36.00 ± 4.76 bc |
| 16.67 | −4.24 (0.0017) | −4.56 (0.0010) | −4.69 (0.0009) | −4.18 (0.0019) | −2.35 (0.0404) | 35.25 ± 3.47 bc |
| 33.33 | −5.28 (0.0004) | −5.43 (0.0003) | −5.75 (0.0002) | −5.93 (0.0001) | −5.66 (0.0002) | 17.33 ± 7.22 c |
| 66.67 | −5.91 (0.0001) | −5.52 (0.0003) | −6.06 (0.0001) | −5.98 (0.0001) | −4.35 (0.0015) | 24.25 ± 11.99 c |

†t and p values (in parentheses) are represented, df = 5 for each test.
‡Means followed by the same letter are not significantly different (P > 0.05).

Figure 8:
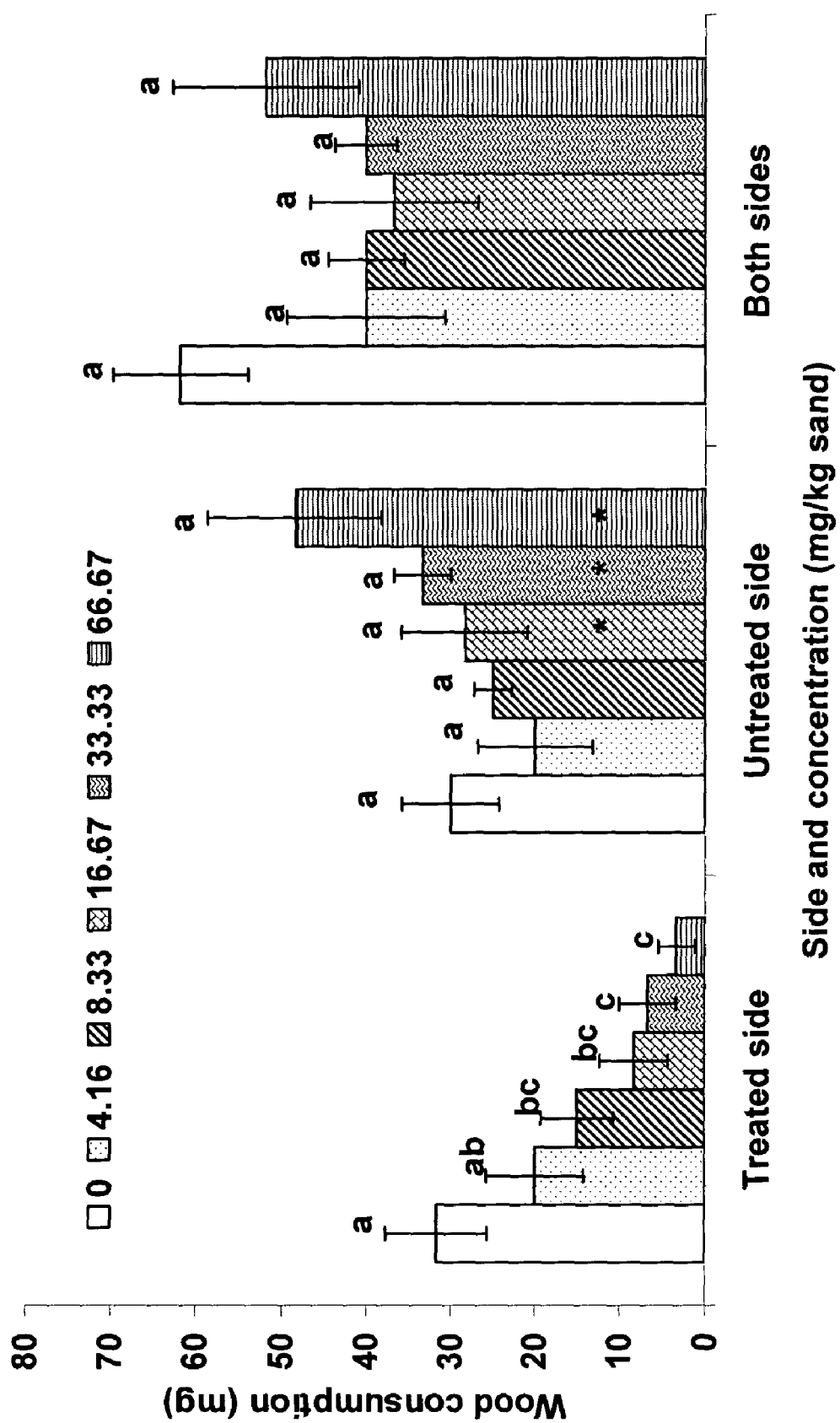
FIG. 8 illustrates the food consumption by C. formosanus workers, measured as the mean loss (±SE) in weight of wood slices placed on the surface of 2'-acetonaphthone-treated (at various concentrations, 4.16 to 66.67 mg/kg sand) and untreated sand during 12 days exposure.

Survival on day 12 was significantly reduced in treatments with ≧8.33 mg/kg 2'-acetonaphthone compared to the control (F=4.89; df=5, 30; P=0.0022; Table 8). Consumption of wood slices placed on the surface of treated sand was significantly reduced in treatments with ≧8.33 mg/kg 2'-acetonaphthone compared to the control (F=5.51; df=5, 30; P=0.001; FIG. 8). FIG. 8 illustrates the weight (mean±SE) of wood slices consumed by *C. formosanus* workers within 12 days exposure to 2'-acetonaphthone-treated and untreated sand. Bars within each group marked by different letters are significantly different (F, P are 5.51, 0.001 (treated side); 2.22, 0.081 (untreated side); and 1.41, 0.2484 (both sides); df values are 5,30 for all). For each concentration, bars marked by an asterisk (*) indicate a significant different in wood consumption between treated and untreated chambers (paired t-tests; Table 8). In contrast, food consumption in the untreated sides was not significantly different from the control in treatments up to 66.6 mg/kg (F=2.22; df=5, 30; P=0.08; FIG. 8). The sum of feeding activity in both treated and untreated sides was also not significantly different in all treatments (F=1.41; df=5, 30; P=0.2484; FIG. 8).

Figure 9:
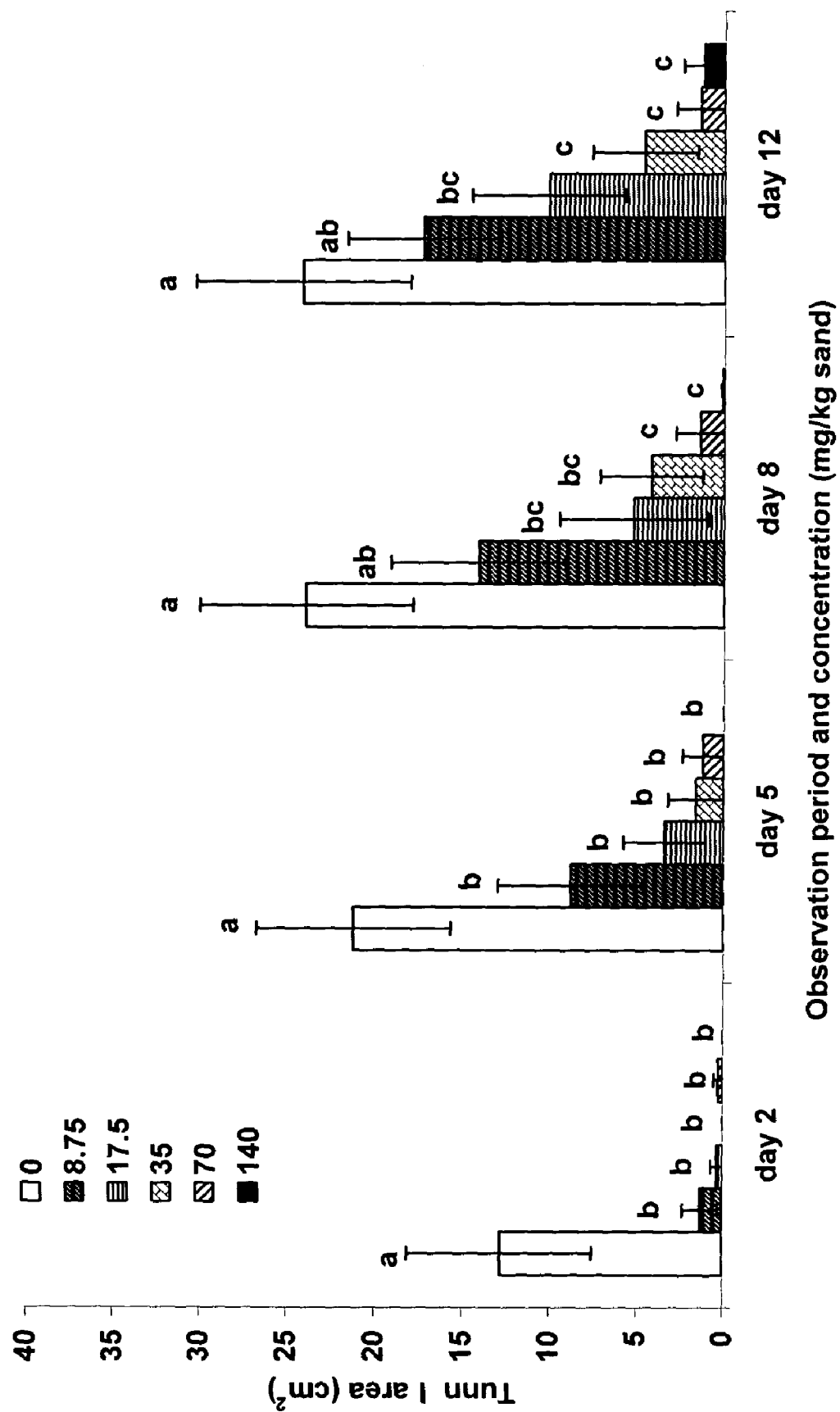
FIG. 9 illustrates the mean tunnel areas (±SE) constructed by C. formosanus workers in 2'-acetonaphthone-treated sand (at various concentrations, 8.75 to 140 mg/kg sand) as measured on days 2, 5, 8, and 12.

The above experiment was repeated with termites from colony E, which had previously indicated a 4-fold greater tolerance toward 2'-acetonaphthone than termites from colony WB. A significant reduction in tunneling activity from the controls was observed in containers with ≧17.5 mg/kg 2'-acetonaphthone-treated sand at all observation periods up to 12 days (FIG. 9). FIG. 9 indicates the areas of tunnels (mean±SE) constructed by *C. formosanus* (Colony E) in 2'-acetonaphthone-treated sand (17.5 to 140 mg/kg sand). For each observation period, bars marked by different letters are significantly different. (F, P values are 5.32, 0.002 (day 2); 6.75, 0.0005 (day 5); 5.53, 0.0016 (day 8); and 5.84, 0.0011 (day 12); df values are 5, 24 for all).

Figure 10:
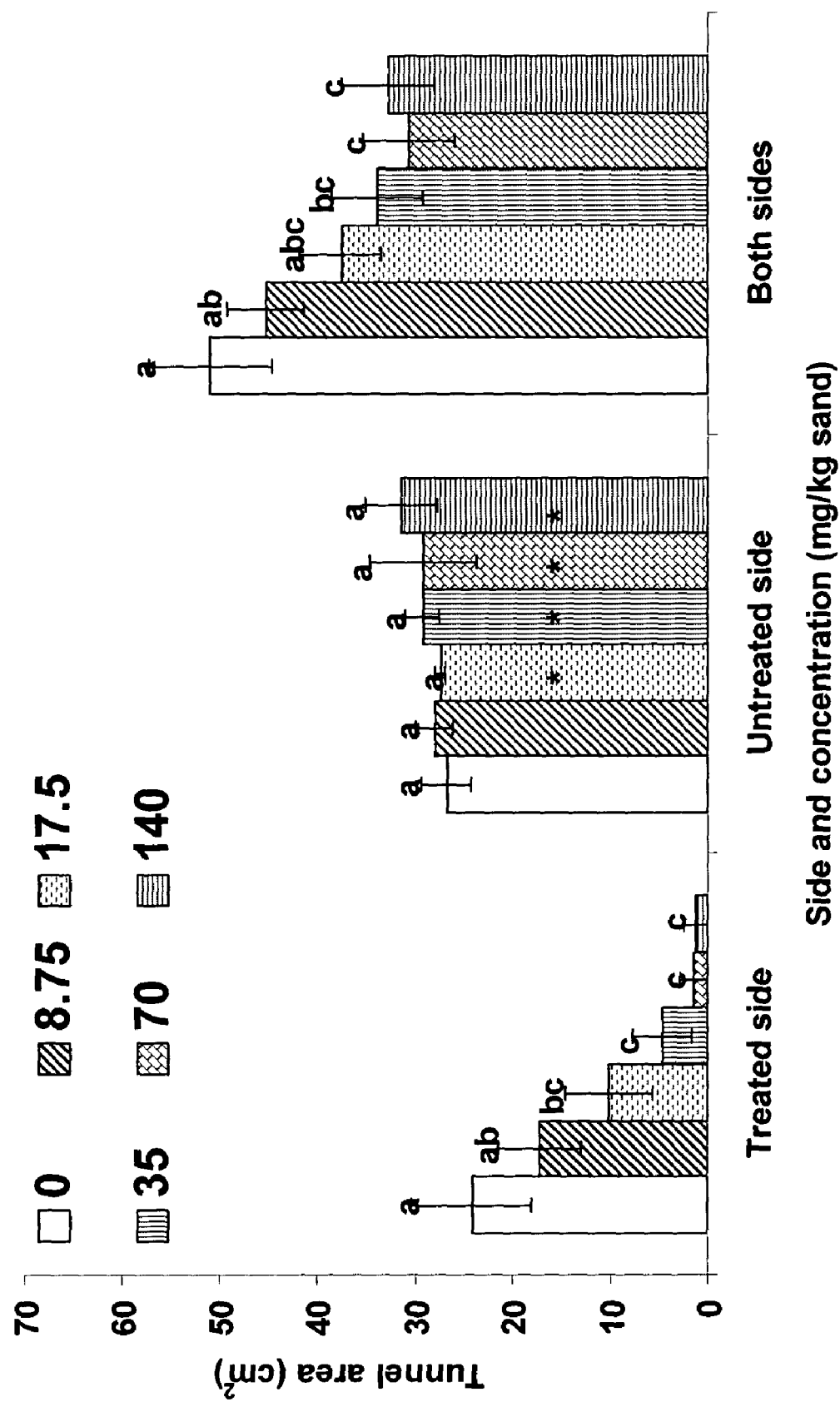
FIG. 10 illustrates the mean tunnel areas (±SE) constructed by C. formosanus workers in 2'-acetonaphthone-treated (at various concentrations, 8.75 to 140 mg/kg sand) and untreated sand as measured after 12 days exposure.

Termites indicated similar tunneling activity in the untreated sand of all experimental containers when compared with the controls (F=0.29; df=5, 24; P=0.9162; FIG. 10). FIG. 10 gives the tunnel area (mean±SE) constructed by termites in 2'-acetonaphthone-treated and untreated sand after a 12-day exposure. For each observation period, bars marked by different letters are significantly different (F, P-values are 5.84, 0.0011 (treated side); 0.29, 0.9162 (untreated side); and 2.78, 0.046 (both sides); df values are 5, 24 for all). For each concentration, bars marked by an asterisk (*) indicate a significant difference in tunnel areas between treated and untreated sand (paired t-tests, Table 9). Significant differences in tunneling activity between treated sand with 2-acetonaphthone concentrations ≧17.5 mg/kg and untreated sand were found (Table 9 and FIG. 10). In addition, treatments of ≧35.0 mg/kg 2'-acetonaphthone significantly reduced overall tunneling as indicated when comparing a sum of tunneling activity in both treated and untreated sand to the same sum in controls (F=2.78; df=5, 24; P=0.0406).

TABLE 9

Paired t-test results for comparing tunneling and feeding activities, and survival of *C. formosanus* (Colony E) in containers with both 2'-acetonaphthone-treated and untreated sand

| Treatment (mg/kg) | t-test values (p value); (df = 4) | | | | | Survival |
|---|---|---|---|---|---|---|
| | Tunnel area, day 2 | Tunnel area, day 5 | Tunnel area, day 8 | Tunnel area, day 12 | Food Consumption, day 12 | (% ± SE)† day 12 |
| 0.0 | −0.59 (0.5731) | 0.97 (0.3615) | 0.25 (0.8080) | 0.40 (0.6962) | −0.21 (0.8417) | 71.80 ± 2.74 a |
| 8.75 | −3.63 (0.0067) | 4.14 (0.0033) | 2.14 (0.0833) | 2.29 (0.0515) | −7.90 (<0.0001) | 61.60 ± 2.79 abc |
| 17.5 | −21.38 (<0.0001) | 8.69 (<0.0001) | 5.16 (0.0009) | 3.91 (0.0045) | −37.95 (<0.0001) | 67.20 ± 1.36 ab |
| 35.0 | −13.63 (<0.0001) | 15.49 (<0.0001) | 7.32 (<0.0001) | 7.04 (<0.0001) | −14.18 (<0.0001) | 59.0 ± 7.72 bc |
| 70.0 | −4.11 (0.0034) | 6.31 (0.0002) | 4.88 (0.0012) | 4.88 (0.0012) | −4.55 (0.0019) | 53.0 ± 2.34 c |
| 140.0 | −5.59 (0.0005) | 12.83 (<0.0001) | 8.64 (<0.0001) | 7.99 (<0.0001) | −5.79 (0.0004) | 51.60 ± 3.97 c |

†Means followed by the same letter are not significantly different (P > 0.05).

Figure 11:
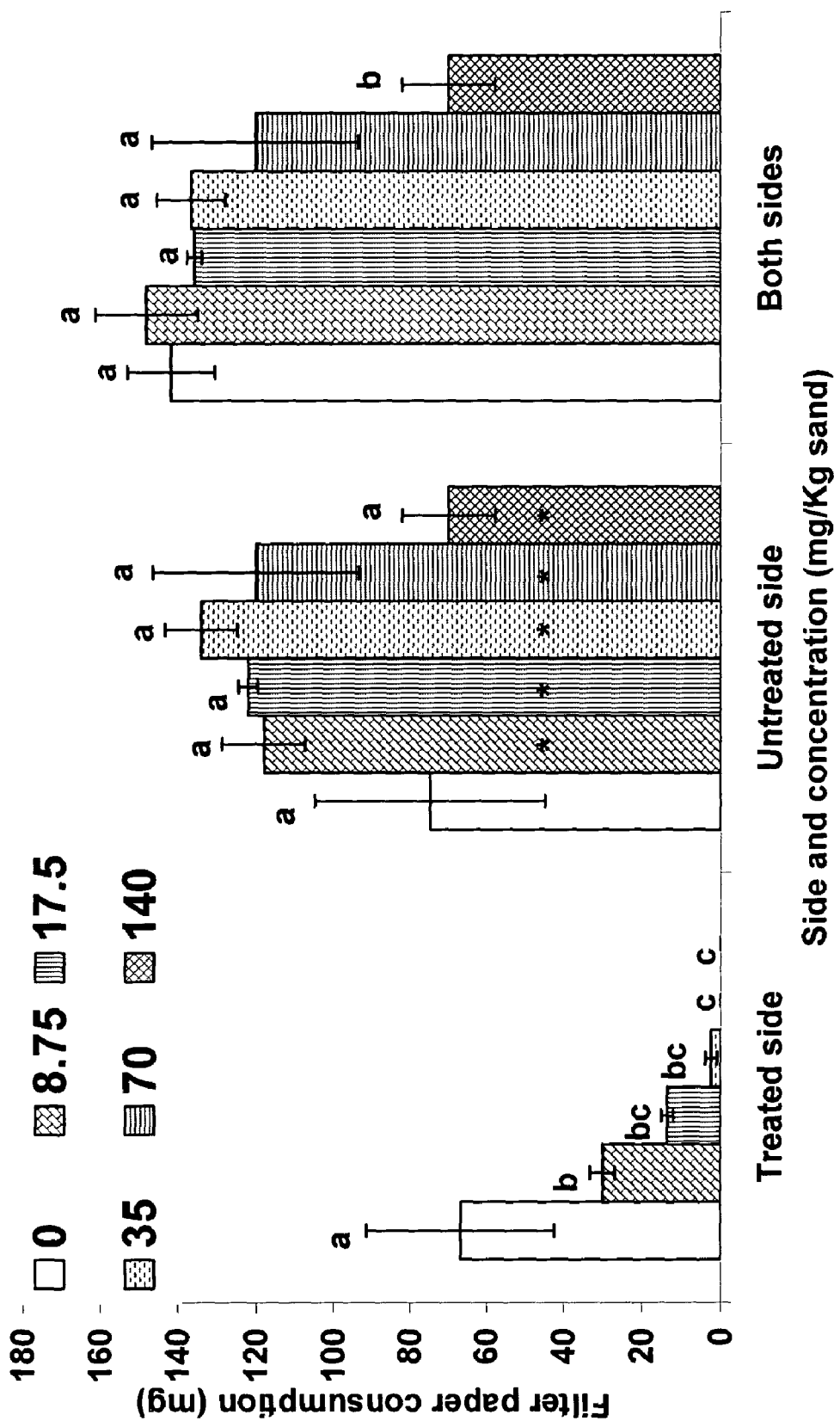
FIG. 11 illustrates the food consumption, measured as the mean loss in weight (±SE) of filter paper placed on the surface of 2'-acetonaphthone-treated (at various concentrations, 8.75 to 140 mg/kg sand) and untreated sand as measured after 12 days exposure.

Survival after 12 days exposure was significantly reduced compared to the control in the containers with treated-sand at concentrations of 2'-acetonaphthone ≧35.0 mg/kg sand. (F=3.79; df=5, 30; P=0.0113; Table 9). Moreover, a significant reduction as compared with control was shown in consumption of filter paper placed on the surface of sand treated with ≧8.75 mg/kg 2'-acetonaphthone (F=6.70; df=5, 24; P=0.0005, FIG. 11). FIG. 11 indicates the weight (mean±SE) of filter paper placed on the surface of 2'-acetonaphthone-treated and untreated sand consumed by *C. formosanus* workers (colony E) after a 12-day exposure. for each side, bars marked by different letters are significantly different (F, P values are 6.7, 0.0005 (treated side); 2.25, 0.0825 (untreated side); and 4.02, 0.0086 (both sides); df values are 5, 24 for all). For each concentration, a bar marked with an asterisk (*) indicates a significant difference in filter paper consumption between treated and untreated sides (paired t-test; Table 9). However, consumption of filter paper placed on the untreated sand in all the 2'-acetonaphthone containers was not significantly different from the control (F=2.25; df=5, 24; P=0.0825, FIG. 11). Total food consumption was significantly less only in 140 mg/kg treatment compared to the control (F=4.02; df=5, 24; P=0.0086; FIG. 11).

Thus, when termites were given the opportunity to choose between 2'acetonaphthone-treated and untreated sand, they avoided the 2'-acetonaphthone-treated sand and stayed in the chamber with untreated sand displaying activity similar to termites in the control container. These data confirm the repellency of 2'-acetonaphthone.

Thus, 2'-acetonaphthone displayed toxic effect on *C. formosanus* when assayed by topical application, treated food sources, and treated sand assays. It was acutely toxic at concentrations <13 μg/termite in a topical application and at 0.1% (wt/v) when applied to a sole food source. The qualitative effect of 2'-acetonaphthone on termite behavior was concentration dependent. In the treated food source assay with an untreated source available, 2'-acetonapththone was repellent at 5 μg/cm$^2$ filter paper, and caused significant reduction in food consumption at ≧20 μg/cm$^2$ filter paper. In contrast, at a 160-fold lower concentrations, 2'-acetonaphthone acted as a feeding stimulant.

The treated sand assays that were used to examine the effects of 2'-acetonaphthone upon the tunneling and feeding behaviors of *Coptotermes formosanus* revealed that 2'-acetonaphthone was a toxicant, repellent, and a molting disruptor to the Formosan subterranean termite. Mortality was found to increase as concentration increased. 2'-Acetonaphthone formed an effective barrier against *C. formosanus*. It was a strong repellent when termites was given a choice of treated and untreated areas. Moreover, it was a stronger inhibitor of tunneling and feeding behaviors of Formosan subterranean termites at a much lower concentration (≧8.33 mg/kg) compared to other tested naturally occurring compounds, e.g., azadirachtin (500 mg/kg; the active component of neem oil) and nootkatone (100 mg/kg; the active component of Alaskan yellow cedar).

EXAMPLE 7

Efficacy of Naphthalene and 10 Related Compounds Against Termites

The effectiveness of 2'-acetonaphthalone led to the evaluation of other naphthalene-related compounds for toxicity and repellency against termites. The structures of naphthalene and the related compounds are given in FIG. 1. The chemicals were tested in assays similar to those described above. Of the eleven chemicals tested, the most effective compounds were 1'-acetonaphthone, 2'-acetonaphthone, 1-methoxynapthalene, and 2-methoxynaphthalene. These four chemicals were effective toxicants at concentrations ranging from 7.1 to 73.2 ug/cm$^2$ filter paper, when the LC$_{90}$ was based on 24 hr mortality data when the treated filter paper was the sole food source. However, 1'- and 2'-acetonaphthone were more toxic than 1- and 2-methoxynaphthalene. In assays with treated sand only, all four chemicals were toxicants at concentrations ≧100 mg/kg sand with 1' and 2'-acetonaphthone being more effective. (Data not shown)

When termites were given a choice of treated or untreated food or sand, all four chemicals were repellents at concentrations of 40 μg/cm$^2$ treated filter paper or 100 mg/kg treated sand. The methoxynaphthalenes were more potent than the acetonaphthalones in reducing termite survival and food consumption even in the untreated sides. Methoxynaphthalenes were more volatile than acetonaphthones and could spread more effectively into the untreated chambers. Napthalene was toxic at higher concentrations (274 to 548 μg/cm$^2$), but did not show any repellency up to 500 μg/cm$^2$. (Data not shown)

Of the eleven chemicals tested and shown in FIG. 1, 1'- and 2'-acetonaphthone had the highest longevity and lowest volatility. Both were also the most effective toxicants and repellents. At concentrations as low as 8 mg/kg sand, 2'-acetonapththone reduced tunneling and feeding activity in termites. There was also an indication that 2'-acetonaphthone inhibited normal molting. Thus these naphthalene derivatives could be added to substrate or food sources to inhibit molting at lower concentrations than that required to kill the termites prior to molting.

The naphthalene derivative, 2'-acetonaphthone, at very low concentrations (about 0.125 μg/cm$^2$) was found to stimulate feeding. Thus these naphthalene derivatives could be added to a bait source to increase the feeding of termites on the bait. These bait sources could contain toxicants, such as hexaflumuron, chlorofluazuron, diflubenzuron, or other insect growth regulators.

In the specification and claims, an effective amount of either 1'-acetonaphthalone, 2'-acetonaphthone, 1-methoxynaphthalene, or 2-methoxynapththalene is defined to be an amount that, when applied to a substrate or other material, causes significant effect on termites (e.g., repellency, toxicity, molting inhibition, or feeding stimulation) as compared to an otherwise identical substrate or material without the addition of either 1'-acetonaphthalone, 2'-acetonaphthone, 1-methoxynaphthalene, or 2-methoxynapththalene.

The complete disclosures of all references cited in this specification are hereby incorporated by reference. Also incorporated by reference are the complete disclosures of the following unpublished transcripts: S. A. Ibrahim et al., "Tunneling and feeding behaviors of *Coptotermes formosanus* (Isoptera: Rhinotermitidae) in response to 2'-acetonaphthone-treated sand," submitted to Pest Management Science, Apr. 2, 2003; and S. A. Ibrahim et al., "Toxic, repellent, deterrent, and stimulant effects of 2'-acetonaphthone on *Coptotermes formosanus* (Isoptera: Rhinotermitidae)," submitted to Pest Management Science, Jun. 6, 2003. In the event of an otherwise irreconcilable conflict, the present specification shall control.

We claim:

1. A method for the killing of termites, comprising the step of treating said termites with an effective amount of a compound selected from the group comprising 1'-acetonaphthone, 2'-acetonaphthone, 1-methoxynaphthalene, and 2-methoxynaphthalene; wherein the mortailty of the termites is substantially greater compared to the mortally of the termites without the added compound.

2. A method as in claim 1, wherein the compound is 1'-acetonaphthone.

3. A method as in claim 1, wherein the compound is 2'-acetonaphthone.

4. A method as in claim 1, wherein the compound is 1-methoxynaphthalene.

5. A method as in claim 1, wherein the compound is 2-methoxynaphthaiene.

6. A method as in claim 3, wherein the termites are treated with an amount of 2'-acetonaphthone greater than 2 µg/termite.

7. A method as in claim 6, wherein the termites are treated with an amount of 2'-acetonaphthone of about 13 µg/termite.

8. A method as in claim 1, wherein the termites are killed due to the inability to molt.

* * * * *